(12) United States Patent
Hanafusa et al.

(10) Patent No.: US 10,473,630 B2
(45) Date of Patent: Nov. 12, 2019

(54) PREPROCESSING KIT, PREPROCESSING APPARATUS USING SAID PREPROCESSING KIT TO PREPROCESS SAMPLE, AND ANALYSIS SYSTEM PROVIDED WITH SAID PREPROCESSING APPARATUS

(71) Applicant: SHIMADZU CORPORATION, Kyoto-shi, Kyoto (JP)

(72) Inventors: Nobuhiro Hanafusa, Kyoto (JP); Kenichi Kitamura, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 284 days.

(21) Appl. No.: 15/327,250

(22) PCT Filed: Sep. 2, 2014

(86) PCT No.: PCT/JP2014/072979
§ 371 (c)(1),
(2) Date: Jan. 18, 2017

(87) PCT Pub. No.: WO2016/017042
PCT Pub. Date: Feb. 4, 2016

(65) Prior Publication Data
US 2017/0168027 A1 Jun. 15, 2017

(30) Foreign Application Priority Data
Jul. 28, 2014 (JP) .................................. 2014-152511

(51) Int. Cl.
*C12M 1/00* (2006.01)
*G01N 30/06* (2006.01)
(Continued)

(52) U.S. Cl.
CPC ............... *G01N 30/06* (2013.01); *G01N 1/10* (2013.01); *G01N 30/00* (2013.01); *G01N 35/025* (2013.01);
(Continued)

(58) Field of Classification Search
None
See application file for complete search history.

(56) References Cited

U.S. PATENT DOCUMENTS 4,810,471 A 3/1989 Wachob et al.
4,974,458 A 12/1990 Koike
(Continued)

FOREIGN PATENT DOCUMENTS

JP 57-57348 U 4/1982
JP 63-171337 A 7/1988
(Continued)

OTHER PUBLICATIONS

Communication dated Mar. 5, 2018 from the European Patent Office in counterpart Application No. 14898384.4.
(Continued)

*Primary Examiner* — Kathryn Wright
(74) *Attorney, Agent, or Firm* — Sughrue Mion, PLLC

(57) ABSTRACT

A preprocessing kit includes a separation device, a collecting container, and a skirt part. The skirt part is integrated with the separation device, and is provided to surround an outer circumferential surface of the separation device with a clearance being left from the outer circumferential surface so that a space having a closed upper side and an open lower side is formed between the outer circumferential surface of the separation device and the skirt part. The skirt part is provided in such a way that a lower end of the skirt part comes into intimate contact with a peripheral surface of an opening of the recess part when the collecting container
(Continued)

containing the lower end of the separation device is fitted into the recess part.

15 Claims, 18 Drawing Sheets

(51) Int. Cl.
  *G01N 1/10* (2006.01)
  *G01N 30/00* (2006.01)
  *G01N 35/04* (2006.01)
  *G01N 35/02* (2006.01)
  *G01N 30/02* (2006.01)
  *G01N 1/40* (2006.01)
  *G01N 35/00* (2006.01)

(52) U.S. Cl.
  CPC .............. *G01N 35/04* (2013.01); *C12M 1/00* (2013.01); *G01N 2001/4088* (2013.01); *G01N 2030/027* (2013.01); *G01N 2035/00485* (2013.01)

(56) References Cited

U.S. PATENT DOCUMENTS

| | | | | |
|---|---|---|---|---|
| 2001/0001643 | A1* | 5/2001 | Simpson | B01L 3/50255 422/400 |
| 2008/0131328 | A1* | 6/2008 | Schutt | B01L 9/06 422/400 |
| 2011/0104026 | A1 | 5/2011 | Yoon et al. | |
| 2011/0291004 | A1 | 12/2011 | Kanda et al. | |
| 2012/0121464 | A1 | 5/2012 | Nogami et al. | |
| 2012/0134895 | A1 | 5/2012 | Kanda et al. | |
| 2015/0051383 | A1* | 2/2015 | Doucette | G01N 1/4077 530/419 |

FOREIGN PATENT DOCUMENTS

| | | |
|---|---|---|
| JP | 01-250071 A | 10/1989 |
| JP | 04-099477 A | 3/1992 |
| JP | 2002-531258 A | 9/2002 |
| JP | 2003-339374 A | 12/2003 |
| JP | 2006-007081 A | 1/2006 |
| JP | 2006-284604 A | 10/2006 |
| JP | 2007-024621 A | 2/2007 |
| WO | 2010/087387 A1 | 8/2010 |
| WO | 2011/019032 A1 | 2/2011 |
| WO | 2013/166605 A1 | 11/2013 |

OTHER PUBLICATIONS

Communication dated Dec. 3, 2018, from European Patent Office in counterpart application No. 14898384.4.
International Search Report for PCT/JP2014/072979 dated Dec. 9, 2014.
Communication dated Oct. 17, 2017, from the Japanese Patent Office in counterpart application No. 2016-537711.
Communication dated Sep. 4, 2018 from the State Intellectual Property Office of P.R.C. in counterpart application No. 201480080617.7.
Notice of Reasons for Refusal dated May 21, 2019 issued by the Japanese Patent Office in counterpart application No. 2018-088054.

* cited by examiner

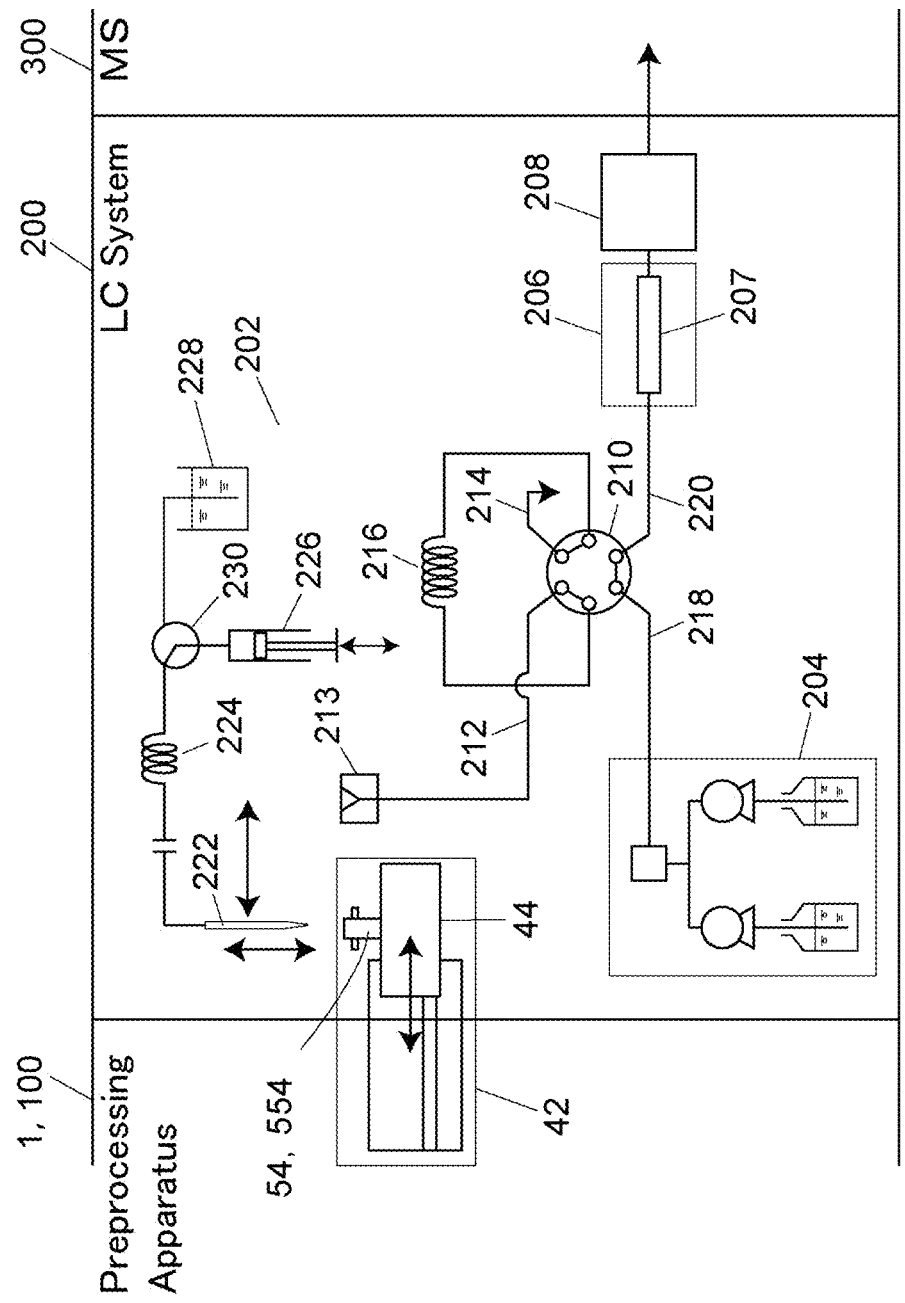

PREPROCESSING KIT, PREPROCESSING APPARATUS USING SAID PREPROCESSING KIT TO PREPROCESS SAMPLE, AND ANALYSIS SYSTEM PROVIDED WITH SAID PREPROCESSING APPARATUS

CROSS REFERENCE TO RELATED APPLICATIONS

This application is a National Stage of International Application No. PCT/JP2014/072979 filed Sep. 2, 2014, claiming priority based on Japanese Patent Application No. 2014-152511 filed Jul. 28, 2014, the contents of all of which are incorporated herein by reference in their entirety.

TECHNICAL FIELD

The present invention relates to: a preprocessing kit for performing preprocessing such as extraction processing in which a specific component unnecessary for analysis, out of components contained in a sample of biological origin such as whole blood, serum, blood plasma, or blood in a filter paper, or urine, is removed, and a necessary component is extracted as a sample; a preprocessing apparatus which automatically performs preprocessing by using the preprocessing kit; and an analysis system which includes the preprocessing apparatus and automatically performs a series of processing from preprocessing of a sample to analysis.

BACKGROUND ART

In performing quantitative analysis on a sample such as a sample of biological origin, processing of removing a specific component unnecessary for analysis from the sample of biological origin and extracting a necessary component as a sample, and drying/solidifying processing of concentrating or drying/solidifying an extracted sample, should be performed in some cases. Conventionally, various apparatuses each serving as a preprocessing apparatus which automatically performs the above-stated preprocessing have been proposed and implemented (for example, refer to Patent Document 1).

For example, Patent Document 1 discloses that a plurality of cartridges holding a separation agent for dipping a sample and separating a specific component from the sample are held by a common carrying mechanism, the cartridges are sequentially placed in a pressure applying mechanism provided in a predetermined position by the carrying mechanism, and a pressure is applied to the cartridges in the pressure applying mechanism so that the sample is extracted. In this case, a plurality of extract receivers which receive extracts from the cartridges are moved relative to the cartridges below the cartridges by another carrying mechanism different from the carrying mechanism for the cartridges, to be sequentially placed in the pressure applying mechanism, so that extraction of the sample is successively performed.

PRIOR ART DOCUMENTS

Patent Documents

Patent Document 1: Japanese Patent Laid-open Publication No. 2010-60474

SUMMARY OF THE INVENTION

Problems to be Solved by the Invention

In the above-described method, the carrying mechanisms for the cartridges and the extract receivers cannot be moved while extraction processing of a sample is performed in the pressure applying mechanism. For this reason, an operation of taking out an extracted sample, or similar operations, cannot be performed during extraction processing of a sample, so that there is a limit to what can be done for improving efficiency in preprocessing. Further, it is not easy to take a sample which is extracted to be in an extract receiver because the extract receiver is always placed below the cartridges.

In view of the foregoing matters, it is an object of the present invention to make it easy to take out a sample extracted by preprocessing, and improve efficiency in preprocessing of a sample.

Solutions to the Problems

A preprocessing kit, according to the present invention, is prepared for each sample, is individually carried to, and set in, a port for performing preprocessing in a preprocessing apparatus which performs preprocessing, and is used for performing preprocessing independently in each port. The preprocessing kit includes a separation device, a collecting container, and a skirt part. The separation device is a cylindrical container which has an internal space which is upwardly open, and includes: a separation layer which allows a sample to penetrate and separates a specific component in the sample from the sample, in the internal space; and an extraction outlet for extracting the sample penetrating the separation layer, in a lower end. The collecting container has an opening which is upwardly open, is attachable to and detachable from the separation device by insertion of a lower portion of the separation device into the opening, has an internal space in which the sample extracted to be provided from the extraction outlet of the separation device is collected, and is fitted into a recess part forming a filtration port for performing extraction processing on a sample with the lower end of the separation device being contained in the internal space. The skirt part is integrated with the separation device, is provided so as to surround an outer circumferential surface of the separation device with a clearance being left from the outer circumferential surface so that a space having a closed upper side and an open lower side is formed between the outer circumferential surface of the separation device and the skirt part. The skirt part is provided is such a way that a lower end of the skirt part comes into intimate contact with a peripheral surface of an opening of the recess part when the collecting container containing the lower end of the separation device is fitted into the recess part.

A preprocessing apparatus according to the present invention is an apparatus which performs preprocessing by using the preprocessing kit according to the present invention. The preprocessing apparatus includes: a carrying mechanism which includes a holding part holding a separation device and/or a collecting container of the preprocessing kit, and moves the holding part, to carry the separation device and/or the collecting container; a filtration part which includes a filtration port including a recess part in which the collecting container containing a lower end of the separation device is contained, in a position along a track of the holding part, and a pressure applying part which causes a negative pressure to be maintained in the filtration port where the preprocessing kit is set; and a controller which controls operations of the carrying mechanism and the pressure applying part. The controller includes a preprocessing means which is configured to set the separation device containing a sample to be subjected to filtration processing and the collecting container for collecting an extracted sample provided from the separation device in the filtration port, and to perform extraction processing on a sample in the filtration port while causing a negative pressure to be maintained in the filtration port.

An analysis system according to the present invention includes: the preprocessing apparatus according to the present invention; a transfer apparatus which is provided in the preprocessing apparatus, and includes a transfer port for setting a collecting container containing a preprocessed sample with a carrying mechanism of the preprocessing apparatus, and a driving mechanism which moves the transfer port to an outside of the preprocessing apparatus; and a liquid chromatograph system which is placed adjacent to the preprocessing apparatus. The liquid chromatograph system includes: an analytical flow path through which a mobile phase flows; a sample injecting apparatus which takes a sample in the collecting container set in the transfer port which is placed outside the preprocessing apparatus by the transfer apparatus, and injects the sample into the analytical flow path; an analytical column which is placed on the analytical flow path and separates the sample injected by the sample injecting apparatus into individual components; and a detector which detects a sample component separated in the analytical column.

Effects of the Invention

The preprocessing kit, according to the present invention, is prepared for each sample, is individually carried and set in a port for performing preprocessing in a preprocessing apparatus which performs preprocessing, and is subjected to preprocessing independently in each port, so that preprocessing such as sample-extraction processing can be performed on a plurality of samples in parallel and concurrently, which improves efficiency in preprocessing. The preprocessing kit includes a separation device and a collecting container which can be attached to or detached from each other, so that the separation device and the collecting container can be separated after a sample is extracted to be provided from the separation device to the collecting container, which makes it easy to take out an extracted sample. Further, the preprocessing kit includes a skirt part which is integrated with the separation device, and is provided so as to surround an outer circumferential surface of the separation device with a clearance being left from the outer circumferential surface so that a space having a closed upper side and an open lower side is formed between the outer circumferential surface of the separation device and the skirt part. The skirt part is provided in such a way that a lower end of the skirt part comes into intimate contact with a peripheral surface of an opening of a recess part forming a filtration port when the collecting container containing a lower end of the separation device is fitted into the recess part. Thus, it is possible to provide an enclosed space in the filtration port only by setting the preprocessing kit in the filtration port, which makes it easy to decompress the filtration port so that a negative pressure is maintained therein. Since an opened upper surface of the separation device is open to air, to set the preprocessing kit and cause a negative pressure to be maintained in the filtration port would result in that a sample penetrates the separation layer and is filtered due to a difference in pressure between a portion above the separation layer and a portion below the separation device in the separation device, so that the sample is extracted to be in the collecting container.

The preprocessing apparatus according to the present invention, includes: a carrying mechanism which includes a holding part holding a separation device and/or a collecting container of a preprocessing apparatus, and moves the holding part to carry the separation device and/or the collecting container; and a filtration part which includes a filtration port having an inner diameter larger than an outer diameter of the collecting container and including a recess part which contains the collecting container containing a lower end of the separation device with a clearance being left from the outer circumferential surface of the collecting container, in a position along a track of the holding part, and a pressure applying part which causes a negative pressure to be maintained in a filtration port when a preprocessing kit is set. Thus, the separation device and/or the collecting container of the preprocessing kit, which individually contains a sample, can be carried individually, and sample-extraction processing (which will be also referred to as "filtration processing") can be performed individually in the filtration port. As a result of this, preprocessing can be performed on a plurality of samples in parallel and concurrently, which improves efficiency in preprocessing of a sample. The term, "to carry a separation device and/or a collecting container" means, both, to carry one of a separation device and a collecting container, and to carry both of a separation device and a collecting container.

In the analysis system according to the present invention, a liquid chromatograph system is set adjacent to the preprocessing apparatus according to the present invention, and a sample injecting apparatus of the liquid chromatograph system is configured to take a sample from a collecting container which is placed outside the preprocessing apparatus by a transfer apparatus provided in the preprocessing apparatus, and analyze the sample, so that a whole series of processing from preprocessing of a sample to analysis can be automatically performed.

BRIEF DESCRIPTION OF THE DRAWINGS

FIG. 14 is a flow-path configuration diagram showing a configuration of a liquid chromatograph system in the embodiment.

EMBODIMENTS OF THE INVENTION

Figure 1:
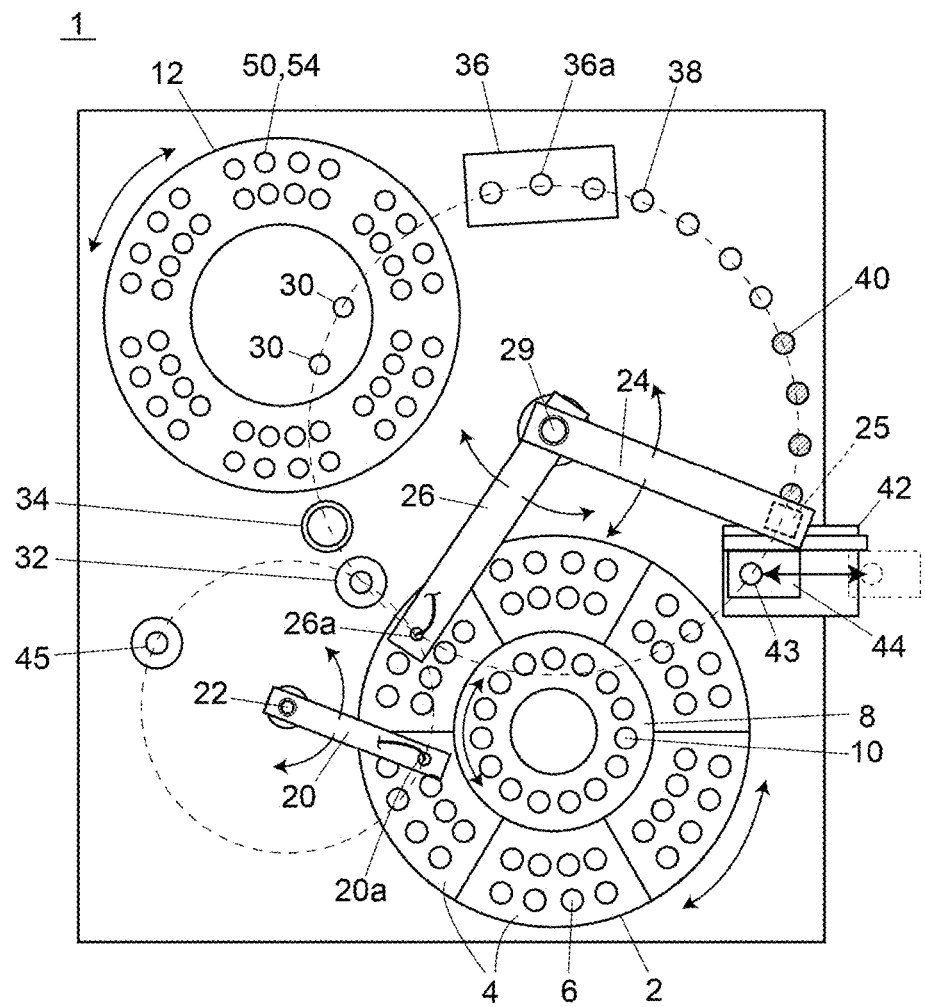
FIG. 1 is a plan view showing one embodiment of a preprocessing apparatus.

In a preprocessing kit according to the present invention, preferably, a separation device includes a flange part which is a circumferential expansion of an outer circumferential surface of the separation device above a skirt part, and a collecting container includes a flange part which is a circumferential expansion of an outer circumferential surface of a portion above a portion which is to be fitted into a recess part forming a filtration port. This makes it easy to hold each of the separation device and the collecting container, so that a configuration of a holding part of a carrying mechanism which carries the separation device and the collecting container can be simplified.

In the above-described case, regarding the separation device, preferably: an outer diameter of a lower portion of the device which is a portion located below a base portion of the skirt part is smaller than an outer diameter of an upper portion of the device which is a portion located above the base portion of the skirt part; an outer circumferential surface of the upper portion of the device is provided with the flange part, so that the lower portion of the device is contained in the collecting container; an outer diameter of an upper portion of the container in the collecting container into which the lower portion of the device is inserted, is identical to an outer diameter of the upper portion of the device; a flange part is provided in the upper portion of the container; and the flange part of the separation device and the flange part of the collecting container have the same shape and the same dimension. This allows the separation device and the collecting container to be carried by the carrying mechanism in common.

Meanwhile, when the lower portion of the separation device is inserted into the collecting container so that the separation device and the collecting container are integrated with each other, an upper portion of the collecting container is inserted into the skirt part. At that time, if an upper end of the collecting container and a base portion of the skirt part come into intimate contact with each other, or if a clearance therebetween is small, a pressure in the collecting container cannot be efficiently reduced in spite of suction of air outside the collecting container. Thus, a notch which is upwardly open may be provided at an edge of an opening in an upper portion of the collecting container. To provide the notch which is upwardly open at an edge of an opening in an upper portion of the collecting container would provide an opening which allows circulation of air when the upper portion of the collecting container is inserted into the skirt part, so that a pressure in the collecting container can be efficiently reduced.

As a separation layer provided in the separation device, a deproteinizing filter for removing protein in a sample, or a layer including a deproteinizing filter and a prefilter which is provided above the deproteinizing filter and prevents clogging in the deproteinizing filter, is cited.

In the preprocessing apparatus according to the present invention, preferably, a collecting-container holding member which comes into contact with an outer circumferential surface of the collecting container, to elastically deform in a direction perpendicular to the outer circumferential surface when the collecting container is fitted into the filtration port, and holds the collecting container in a central portion of the filtration port while uniformly pressing the outer circumferential surface of the collecting container from a periphery of the collecting container, is provided in an inner side surface of a carrying/filtration port. This stabilizes positions of the separation device and the collecting container which are set in the filtration port, so that a possibility that the holding part of the carrying mechanism may fail to hold the separation device or the collecting container can be reduced.

An example of the collecting-container holding member includes plate springs provided in plural positions which are circumferentially arranged and are evenly spaced from each other in an inner side surface of the filtration port.

Preferably, in a portion which surrounds an opening of the recess part forming the filtration port and comes into contact with a lower end of the skirt part of the preprocessing kit, a sealing member formed of an elastic material which enhances adherence to the lower end of the skirt part is provided. This improves hermeticity in the filtration port when the preprocessing kit is set in the filtration port, which facilitates decompression of the filtration port.

Preferably, a processing means included in a controller is configured to press the separation device downward with the holding part of the carrying mechanism after setting the separation device and the collecting container in the filtration port. Thus, at a start of filtration process, a lower end of the skirt part of the separation device is pressed against a periphery of the filtration port, which enhances hermeticity in the filtration port, so that the filtration port can be easily decompressed. After a negative pressure is maintained in the filtration port, the filtration port is kept under a negative pressure without continuing pressing the separation device downward, so that the carrying mechanism is allowed to perform other operations.

Preferably, a plurality of filtration ports are included, the pressure applying part is configured to make a pressure in each of the filtration ports negative. Further, the controller further includes a processing-state control means which controls a state of filtration processing in the filtration ports and availability of each of the filtration ports; and a random access means which is configured to check availability of the filtration ports when a sample which should be subjected to filtration processing is provided, and set a separation device containing the sample and a collecting container collecting an extract of the sample in an available filtration port if there is any available filtration port. This makes it possible to perform sample-extraction processing in parallel and concurrently, but individually, while sequentially setting preprocessing kits each containing a sample in available filtration ports as soon as the filtration ports become available, so that a throughput in preprocessing is improved.

As an example of the carrying mechanism, cited is a carrying arm which horizontally extends, has a base end pivotally supported by a shaft extending vertically, and is configured to rotate about the shaft in a horizontal plane, and vertically move along the shaft. In such a case, the filtration port is provided in a position along a circumferential track which is made by the holding part along with rotation of the carrying arm. As a result of the above-described configuration, a configuration of the carrying arm can be simplified.

In the above-described case, preferably, included are: a dispensation port for setting the separation device to which a sample or a reagent should be dispensed; and a stirring port which holds the separation device containing a reagent and a reagent and causes the separation device to periodically move in a horizontal plane so that stirring occurs in the separation device, and those ports are provided in positions along a circumferential track which is made by the holding part along with rotation of the carrying arm. This allows the carrying mechanism including the carrying arm to set the separation device in the dispensation port or the stirring port.

Further, preferably, included is a transfer apparatus which includes: a transfer port holding the collecting container containing a sample component extracted by filtration processing; and a driving mechanism which moves the transfer port to a side where an automatic sample injecting apparatus placed adjacent to the preprocessing apparatus is provided. In this case, the transfer port is provided in a position along a circumferential track which is made by the holding part along with rotation of the carrying mechanism. As a result of this, the carrying arm can set the collecting container containing a sample component extracted by filtration processing, in the transfer port, so that the collecting container can be automatically transferred to the automatic sample injecting apparatus placed adjacent to the preprocessing apparatus. This makes it possible to automate all of processing from preprocessing of a sample to processing for introducing a sample into a liquid chromatograph.

Further, the preprocessing apparatus may be provided with a temperature adjustment port which contains the separation device or the collecting container containing a sample, and adjusts a temperature of the separation device or the collecting container at a certain temperature, the temperature adjustment port being provided in a position along a circumferential track which is made by the holding part along with rotation of the carrying arm. Thus, in a case where a sample should be maintained under conditions of a certain temperature, the separation device or the collecting container containing the sample can be carried to the temperature adjustment port by the carrier arm, and set.

Further, preferably, the preprocessing apparatus is provided with a disposal port for disposing of a separation device or a collecting container which is once used, the disposal port being provided in a position along a circumferential track which is made by the holding part along with rotation of the carrying arm. This allows the carrying arm to automatically dispose of the separation device or the collecting container which is once used.

One embodiment of the preprocessing apparatus will be described with reference to FIG. 1.

A preprocessing apparatus 1 according to this embodiment executes a necessary preprocessing item by using one set of prepared preprocessing kits each including a set of a separation device 50 and a collecting container 54, for each sample. In the preprocessing apparatus 1, a plurality of processing ports for executing respective preprocessing items are provided, and a preprocessing kit containing a sample is set in any of the processing ports so that a preprocessing item corresponding to the processing port is executed on the sample contained in the preprocessing kit. Each of the processing ports will be described later. A preprocessing item is an item of preprocessing which is necessary for executing an analysis item designated by an analyst.

The separation device 50 and the collecting container 54 which form the preprocessing kit are carried by a carrying arm 24 forming a carrying mechanism. The carrying arm 24 includes a holding part 25 for holding the separation device 50 and the collecting container 54 on a tip side, and rotates about a vertical shaft 29 holding a base end of the carrying arm 24, in a horizontal plane in such a manner that the holding part 25 makes an arc-shaped track. All the processing ports and other ports to which the separation device 50 and the collecting container 54 are to be carried are provided along the arc-shaped track made by the holding part 25.

A sample setting part 2 for setting sample containers 6 each containing a sample is provided, and a sampling arm 20 is provided near the sample setting part 2. The sampling arm 20 is a sampling part for taking a sample from a sample container set in the sample setting part 2. In the sample setting part 2, sample racks 4 which hold the plurality of sample containers 6 are annularly arranged. The sample setting part 2 rotates in a horizontal plane so as to circumferentially move the sample racks 4, and a desired one of the sample containers 6 is placed in a predetermined sampling position by rotation of the sample setting part 2. The sampling position is a position along a track of a sampling nozzle 20a provided at a tip of the sampling arm 20, where the sampling nozzle 20a takes a sample.

A vertical shaft 22 penetrates a base end of the sampling arm 20, and the sampling arm 20 rotates about the shaft 22 in a horizontal plane and moves upward and downward in a vertical direction along the shaft 22. The sampling nozzle 20a which is held on a tip side of the sampling arm 20 in such a manner that a tip of the sampling nozzle 20a is oriented vertically downward, is moved so as to make an arc-shaped track in a horizontal plane, and is moved upward and downward in a vertical direction by the sampling arm 20.

A dispensation port 32 is provided in a position on the track of the sampling nozzle 20a and on the track of the holding part 25 of the carrying arm 24. The dispensation port 32 is a port where the sampling nozzle 20a dispenses a sample to the separation device 50 being unused. The separation device 50 being unused is set in the dispensation port 32 by the carrying arm 24.

On an inner side of the sample setting part 2, a reagent setting part 8 for setting a reagent container 10 is provided, and a reagent arm 26 (reagent addition part) for taking a reagent from the reagent container set in the reagent setting part 8, is provided. A base end of the reagent arm 26 is held by the vertical shaft 29 shared with the carrying arm 24, and the reagent arm 26 rotates in a horizontal plane and moves upward and downward. A reagent addition nozzle 26a is provided at a tip of the reagent arm 26 in such a manner that a tip of the reagent addition nozzle 26a is oriented vertically downward, and the reagent addition nozzle 26a moves in a horizontal plane so as to make the same arc-shaped track that the holding part 25 of the carrying arm 24 makes, and moves upward and downward.

The reagent setting part 8 rotates in a horizontal plane independently of the sample setting part 2. In the reagent setting part 8, a plurality of the reagent containers 10 are annularly placed, and as a result of rotation of the reagent setting part 8, the reagent containers 10 are carried in a direction of the rotation, so that a desired one of the reagent containers 10 is placed in a predetermined reagent taking position. A reagent taking position is a position along a track of the reagent addition nozzle 26a of the reagent arm 26, where the reagent addition nozzle 26a takes a reagent. The reagent addition nozzle 26a sucks a predetermined reagent, and then dispenses the sucked reagent to the separation device 50 set in the dispensation port 32, to achieve addition of the reagent to the sample.

A preprocessing-kit setting part 12 is provided in a position different from positions where the sample setting part and the reagent setting part 8 are provided. The preprocessing-kit setting part 12 is configured to allow a plurality of preprocessing kits each including a set of the separation device 50 and the collecting containers 54 which are unused and stacked, to be annularly arranged. The preprocessing-kit setting part 12 rotates in a horizontal plane and moves the preprocessing kits circumferentially, to place a set in an arbitrary preprocessing kit in a position along the track of the holding part 25 of the carrying arm 24. The carrying arm 24 can hold the separation device 50 or the collecting container 54 which is unused and placed in a position along the track of the holding part 25.

An analyst can set plural types (two types, for example) of separation devices 50 in which separation agents having different separation performances are respectively provided, in the preprocessing-kit setting part 12. Those separation devices 50 are used selectively in accordance with each analysis item of a sample, and one of the separation devices 50 which complies with an analysis item designated by the analyst is selected by the preprocessing-kit setting part 12. Appropriate selection of the separation device 50 is achieved by a controller which controls operations of the preprocessing apparatus 1. The controller will be described later. A term "analysis item" in this specification means a kind of analysis which is to be performed by successively using a sample subjected to preprocessing in the preprocessing apparatus 1. As an analysis apparatus which performs such analysis, a liquid chromatograph (LC) or a liquid chromatograph/mass spectrometer (LC/MS) can be cited, for example.

The separation device 50 and the collecting container 54 which form the preprocessing kit will be described with reference to FIGS. 2A, 2B, 2C, and 2D.

Figure 2A:
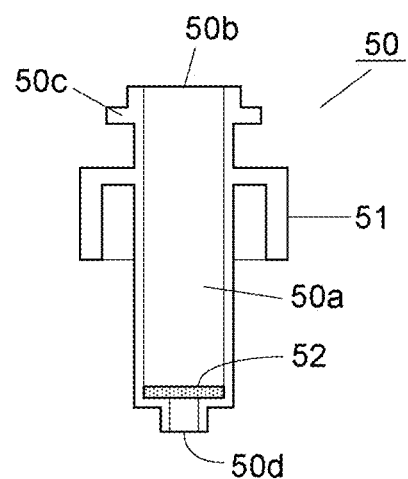
FIG. 2A is a cross-sectional view showing an example of a separation device of a preprocessing kit.

As shown in FIG. 2A, the separation device 50 is a cylindrical container having an internal space 50a in which a sample or a reagent is contained. In a bottom of the internal space 50a, a separation layer 52 is provided. The separation layer 52 is a separation agent or a separation membrane which has a function of separating selectively a specific component in a sample by allowing the sample to penetrate and physically or chemically reacting with the specific component in the sample. As a separation agent forming the separation layer 52, an ion-exchange resin, a silica gel, cellulose, activated carbon, and the like can be used. As a separation membrane, a poly-tetrafluoroethylene (PTFE) membrane, a nylon membrane, a polypropylene membrane, polyvinylidene-difluoride (PVDF) membrane, an acrylic copolymer membrane, a mixed cellulose membrane, a nitro-cellulose membrane, a polyether-sulfone membrane, an ion-exchange membrane, a glass-fiber membrane, and the like, can be used.

Further, as a deproteinizing filter (separation membrane) for removing protein in a sample by filtration, PTFE, an acrylic copolymer membrane, and the like, can be used. In this case, a prefilter 52b may be provided above a deproteinizing filter 52a in order to prevent clogging in the deproteinizing filter, as shown in FIG. 2D. As the prefilter 52b, a nylon membrane, a polypropylene membrane, a glass fiber membrane, and the like, can be used. The prefilter 52b serves to remove an insoluble substance or a foreign substance which has a relatively large particle size, from a sample, and the prefilter 52b can prevent the deproteinizing filter 52a from being clogged with an insoluble substance or a foreign substance which has a relatively large particle size.

In the separation device 50, an opening 50b for injecting a sample or a reagent is provided in an upper surface, and an extraction outlet 50d for extracting a liquid resulted from dipping in the separation agent 52 is provided in a lower surface. Further, a flange part 50c which circumferentially protrudes is provided to be engaged with the holding part 25 of the carrying arm 24 later described, in an upper portion of an outer circumferential surface.

A skirt part 51 which circumferentially protrudes, extends downward by a fixed distance, and surrounds an outer circumferential surface, is provided below the flange part 50c. As will be later described, the skirt part 51 comes into intimate contact with an edge of a filtration port 30 of a processing part 28, to form a sealed space in the skirt part 51 when the skirt part 51 together with the collecting container 54 is contained in the filtration port 30.

Figure 2B:
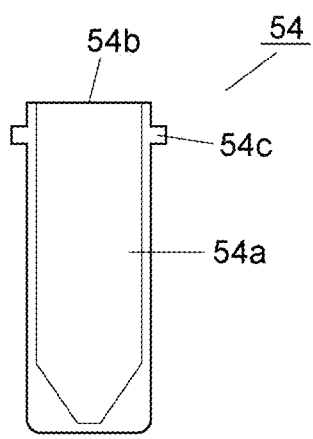
FIG. 2B is a cross-sectional view showing an example of a collecting container of the preprocessing kit.
Figure 2C:
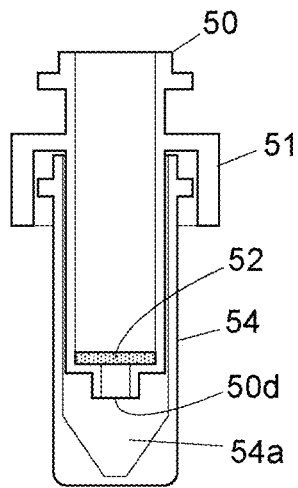
FIG. 2C is a cross-sectional view showing the preprocessing kit in which the collecting container is attached to the separation device.
Figure 2D:
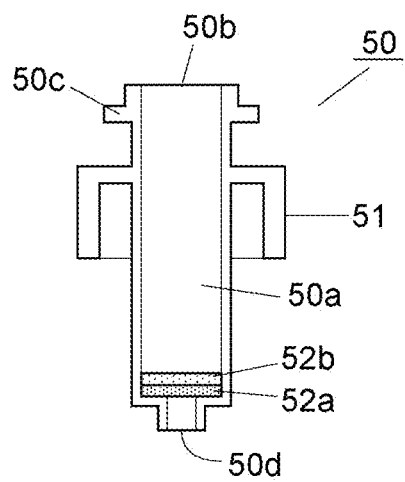
FIG. 2D is a cross-sectional view showing another example of a separation device.

As shown in FIGS. 2B and 2C, the collecting container 54 is a cylindrical container which contains a lower portion of the separation device 50 and collects an extract which is provided from the extraction outlet 50d of the separation device 50. The collecting container 54 includes an opening 54b into which the lower portion of the separation device 50 is inserted, in an upper surface thereof, and also includes a space 54a which contains a portion of the separation device 50 which is located below the skirt part 51. The collecting container 54, similarly to the separation device 50, includes a flange part 54c which circumferentially protrudes to be engaged with the holding part 25 of the carrying arm 24 in an upper portion of an outer circumferential surface thereof. The collecting container 54, similarly to the separation device 50, includes a flange part 54c which circumferentially protrudes to be engaged with the holding part 25 of the carrying arm 24 in an upper portion of an outer circumferential surface thereof. The flange part 54c has the same shape and the same outer diameter as the flange part 50c of the separation device 50. The holding part 25 of the carrying arm 24 can hold the flange part 50c of the separation device 50 and the flange part 54c of the collecting container 54 in a similar fashion.

An upper portion of the collecting container 54 enters into the skirt part 51 when the collecting container 54 is attached to the separation device 50. An outer diameter of the separation device 50 and an inner diameter of the collecting container 54 are designed so as to leave a small clearance between an outer circumferential surface of the separation device 50 and an inner circumferential surface of the collecting container 54 when the separation device 50 is contained in the internal space 54a of the collecting container 54. The separation device 50 and the collecting container 54 are set in the preprocessing-kit setting part 12 with the lower portion of the separation device 50 being contained in the collecting container 54 (in a state shown in FIG. 2C).

Figure 3:
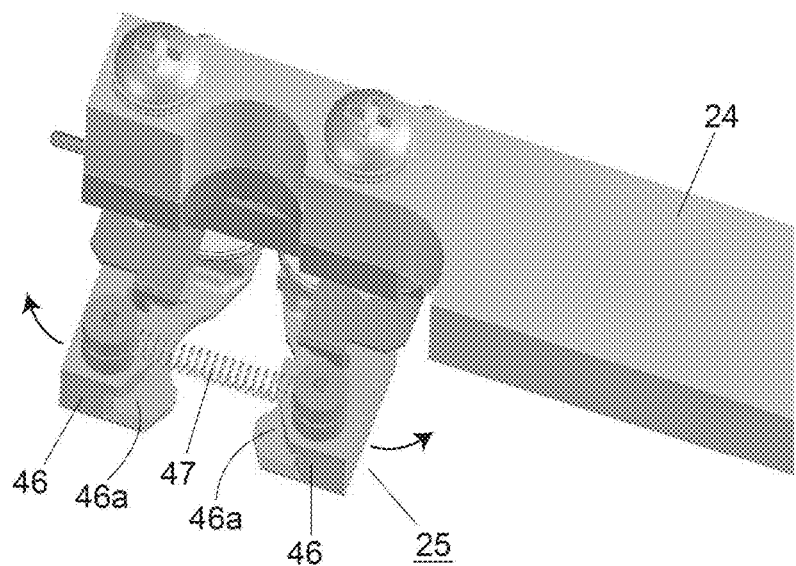
FIG. 3 is a perspective view of a tip of a carrying arm, for showing a structure of a holding part of the carrying arm.

Next, a structure of the holding part 25 of the carrying arm 24 will be described with reference to FIG. 3.

The holding part 25 includes two finger parts 46 which hold the flange part 50c of the separation device 50 or the flange part 54c of the collecting container 54. The finger parts 46 horizontally protrude in a direction substantially perpendicular to the carrying arm 24 at a tip of the carrying arm 24. The two finger parts 46 are spaced from each other and connected with each other via a coil spring 47. The two finger parts 46 can be freely opened and closed in a horizontal direction, and can hold the flange part 50c or 54c of the separation device 50 or the collecting container 54 which is interposed between the finger parts 46, by virtue of an elastic force of the coil spring 47. A groove 46a by which a side edge of the flange part 50c or 54c is slidably held is provided in an inner side surface of each of the two finger parts 46.

The inner side surface of each of the two finger parts 46 has a curved shape so that a distance between the two finger parts 46 is smaller than an outer diameter of a body portion of each of the separation device 50 and the collecting container 54 at a tip, and is almost equal to, or larger than, an outer diameter of the body portion of each of the separation device 50 and the collecting container 54 in a position between a tip and a base end (such a position will be referred to as a "holding position"). Further, the inner side surface of the tip of each of the two finger parts 46 has a smoothly curved shape so that the tip can slide along a shape of the separation device 50 or the collecting container 54 when the finger parts 46 are pushed against the separation device 50 or the collecting container 54. Because of the above-described shape, to simply push the finger parts 46 against the separation device 50 or the collecting container 54 while rotating the carrying arm 24 counterclockwise (left-handed) would automatically open the finger parts 46 along a circumferential surface of the body portion of the separation device 50 or the collecting container 54, and would automatically close the finger parts 46 by virtue of an elastic force of the coil spring 47 when the separation device 50 or the collecting container 54 is located in a holding position between tips and base ends of the finger parts 46, so that the separation device 50 or the collecting container 54 can be stably held.

In order to set the separation device 50 or the collecting container 54 which is being held, in any of the ports, it is required to simply rotate the carrying arm 24 clockwise (right-handed) with the lower portion of the separation device 50 or the collecting container 54 which is being held, being contained in a port where the separation device 50 or the collecting container 54 is to be set. To rotate the carrying arm 24 clockwise with the separation device 50 or the collecting container 54 being contained in a port would automatically open the finger parts 46 along a circumferential surface of the body portion of the separation device 50 or the colleting container 54 because of the curved shape of the inner side surface of each of the two finger parts 46, so that the separation device 50 or the collecting container 54 is released from a hold.

Because of the above-described structure of the holding part 25, an operation for carrying the separation device 50 or the collecting container 54 is performed as follows.

First, the finger parts 46 are placed beside the flange part 50c or 54c of the separation device 50 or the collecting container 54 which is to be carried, and the carrying arm 24 is rotated counterclockwise so that the flange part 50c or 54c slides along the grooves 46a in respective inner side surfaces of the two finger parts 46. As a result of this, the holding part 25 stably holds the flange part 50c or 54c of the separation device 50 or the collecting container 54. Thereafter, the carrying arm 24 is caused to move, and the separation device 50 or the collecting container 54 is set in a port which is a destination.

After the separation device 50 or the collecting container 54 is set in the port which is a destination, the carrying arm 24 is rotated clockwise, so that the separation device 50 or the collecting container 54 is released from a hold. As a result of this, carrying of the separation device 50 or the collecting container 54 is finished, and the separation device 50 or the collecting container 54 is set in the port which is a destination.

Description will be made by referring back to FIG. 1. As processing ports each of which contains a preprocessing kit and is used for executing a specific preprocessing item, filtration ports 30, stirring ports 36a, a temperature adjustment port 38 for the separation device 50, and a temperature adjustment port 40 for the collecting container 54 are provided. The filtration ports 30 are provided in two positions on an inner side of the preprocessing-kit setting part 12. Three stirring ports 36a in a stirring part 36 are provided near the preprocessing-kit setting part 12. Four temperature adjustment ports 38 and four temperature adjustment ports 40 are provided and are aligned on an arc.

Each of the filtration ports 30 is connected with a negative-pressure applying mechanism 55 serving as a pressure applying part (refer to FIGS. 4A and 4B), and the negative-pressure applying mechanism 55 is configured so as to apply a negative pressure to a preprocessing kit set in the filtration port 30. The stirring part 36 includes a mechanism which causes each of the stirring ports 36a to periodically operate in a horizontal plane individually, and serves to stir a sample solution in the separation device 50 placed in each of the stirring ports 36a. Each of the temperature adjustment ports 38 and 40 is provided in a thermally-conductive block, a temperature of which is controlled by a heater and a Peltier element, for example, contains the separation device 50 or the collecting container 54, and adjusts a temperature of the separation device 50 or the collecting container 54 at a certain temperature.

The filtration port 30 will be described with reference to FIGS. 4A, 4B, 4C, and 4D.

Figure 4A:
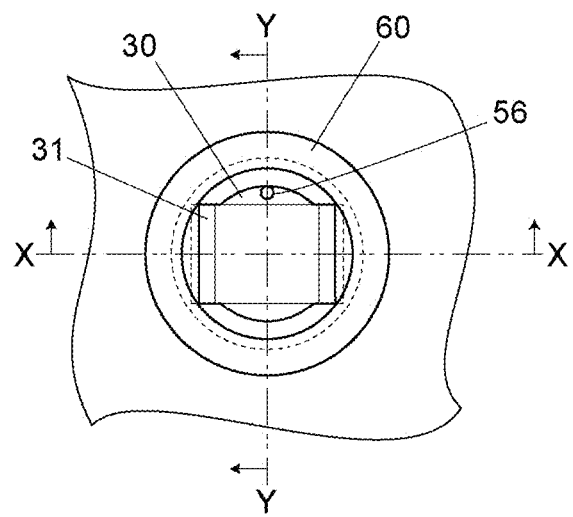
FIG. 4A is a plan view showing a filtration port.

The filtration port 30 includes a recess part which contains the preprocessing kit. As shown in FIG. 4D, the collecting container 54 is contained in the filtration port 30, first, and then a lower portion of the separation device 50 is contained in the internal space 54a of the collecting container 54.

Figure 4B:
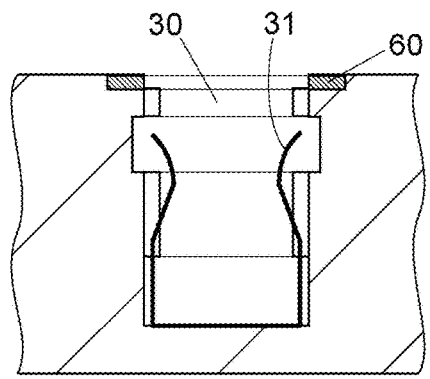
FIG. 4B is a cross-sectional view showing a section "X-X" in FIG. 4A.
Figure 4C:
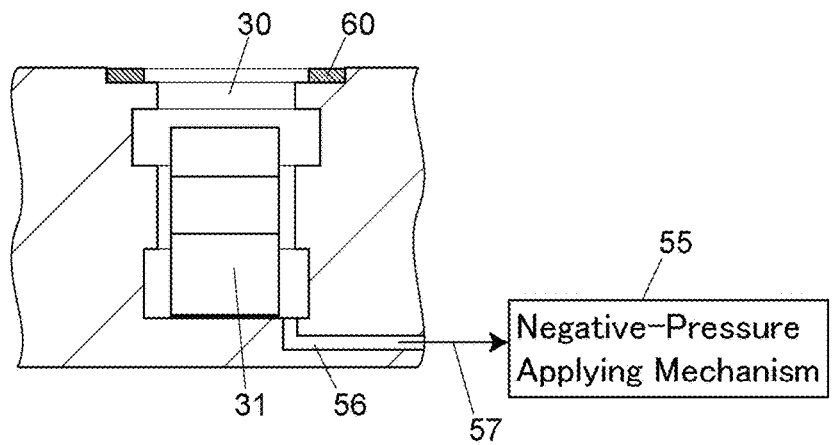
FIG. 4C is a cross-sectional view showing a section "Y-Y" in FIG. 4A.
Figure 4D:
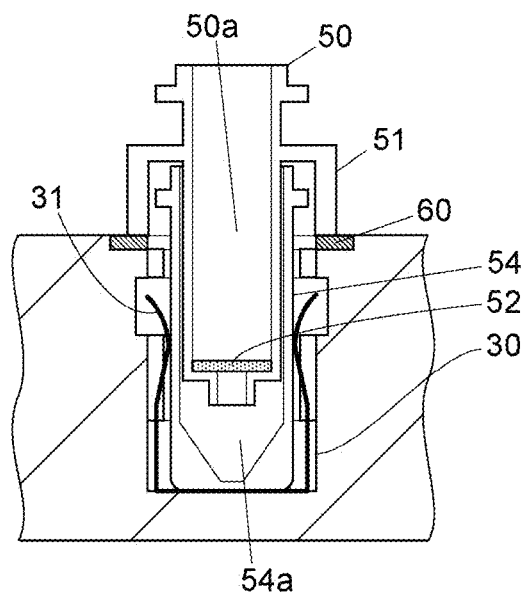
FIG. 4D is a cross-sectional configuration diagram showing a state in which the preprocessing kit is set in a filtration port.

In the filtration port 30, a collecting-container holding member 31 which uniformly presses the collecting container 54 from two directions which face each other across the collecting container 54, and holds the collecting container 54 in a central portion, is provided (refer to FIGS. 4B and 4D). The collecting-container holding member 31 is a U-shaped metal member which is upwardly open, and includes two plate springs configured in such a way that two arms thereof extending upwardly are elastically displaced toward an inner diameter of the filtration port 30. Each of the two plate springs of the collecting-container holding member 31 has a curved-shape or a bent-shape which is inwardly concaved so that a distance between respective portions interposed between upper ends and lower ends of the two plate springs is the smallest. While a distance between respective upper ends or respective lower ends of the two plate springs is larger than an outer diameter of the collecting container 54, a distance between respective portions of the two plate springs, which is the smallest, is smaller than an outer diameter of the collecting container 54. Because of the above-described shape of the collecting-container holding member 31, when the collecting container 54 is inserted into the filtration port 30, the two plate springs of the collecting-container holding member 31 are opened along with a descent of the collecting container 54, and hold the collecting container 54 in a central portion of the filtration port 30 by virtue of an elastic force thereof. The collecting-container holding member 31 is fixed in the filtration port 30, and is prevented from being lifted up together with the collecting container 54 when the collecting container 54 is taken out.

A ring-shaped sealing member 60 having elasticity is provided at an edge of an opening in an upper surface of the filtration port 30. The sealing member 60 is fitted into a depression provided around an edge of an opening in an upper surface of the filtration port 30. A material of the sealing member 60 is an elastic material such as silicon rubber or ethylene-propylene-diene (EPDM) rubber. When the collecting container 54 and the separation device 50 are set in the filtration port 30, a lower end of the skirt part 51 of the separation device 50 comes into contact with the sealing member 60, so that a space surrounded by an inner side surface of the skirt part 51 and an inner side surface of the filtration port 30 is sealed.

A bottom surface of the filtration port 30 communicates with a flow path 56 for decompression (refer to FIGS. 4A and 4C). The flow path 56 is connected with a flow path 57 of a negative-pressure applying mechanism 55. The negative-pressure applying mechanism 55 serves to apply a negative pressure to the filtration port 30 with a vacuum pump, though details of a configuration of the negative-pressure applying mechanism 55 will be provided later.

As a result of the filtration port 30 being decompressed by the negative-pressure applying mechanism 55 with the separation device 50 and the collecting container 54 being contained in the filtration port 30, a negative pressure is maintained in a space surrounded by an inner side surface of the skirt part 51 and an inner side surface of the filtration port 30. The space where a negative pressure is maintained communicates with the internal space 54a of the collecting container 54. Since an upper surface of the separation device 50 is open to air, a difference in pressure is generated between the internal space 50a of the separation device 50 and the internal space 54a of the collecting container 54 with the separation agent 52 being interposed therebetween. Then, only a component which can penetrate the separation agent 52 in a sample solution contained in the internal space 50a of the separation device 50 is extracted to be in the internal space 54a of the collecting container 54 due to the difference in pressure.

Figure 5:
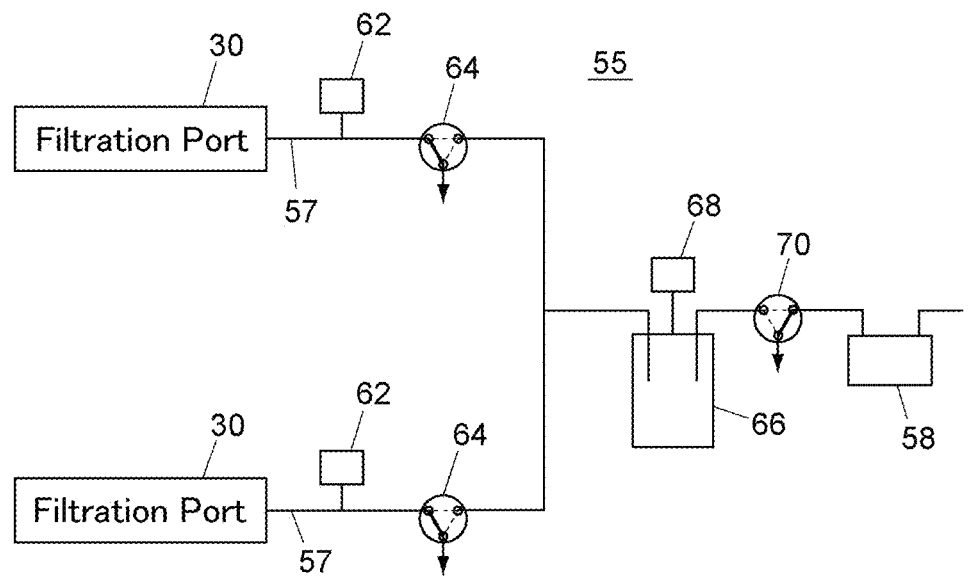
FIG. 5 is a schematic flow-path configuration diagram showing a configuration of a negative-pressure applying mechanism.

FIG. 5 shows an example of the negative-pressure applying mechanism 55.

The two filtration ports 30 are connected with a common vacuum tank 66. Each of the flow paths 57 which connect the filtration ports 30 and the vacuum tank 66, respectively, includes a pressure sensor 62 and a three-way valve 64. The pressure sensor 62 senses a pressure of the filtration port 30. The three-way valve 64 can select a state among a state where the filtration port 30 and the vacuum tank 62 are connected, a state where an end of the flow path 57 closer to the filtration port 30 is open to air (a state shown in FIG. 5), and a state where an end of the flow path 57 closer to the filtration port 30 is sealed.

The vacuum tank 66 is connected with a pressure sensor 68 and is further connected with a vacuum pump 58 via a three-way valve 70, and connection between the vacuum tank 66 and the vacuum pump 58 is established as necessary so that a pressure in the vacuum tank 66 can be adjusted.

In performing extraction processing on a sample in any one of the filtration ports 30, the filtration port 30 is connected with the vacuum tank 66 and a value of the pressure sensor 62 which senses a pressure of the filtration port 30 is adjusted to a predetermined value, and thereafter, an end of the flow path 57 closer to the filtration port 30 is sealed. As a result of this, the filtration port 30 becomes a sealed system, so that an inside of the filtration port 30 is kept decompressed and a sample can be extracted.

Figure 6A:
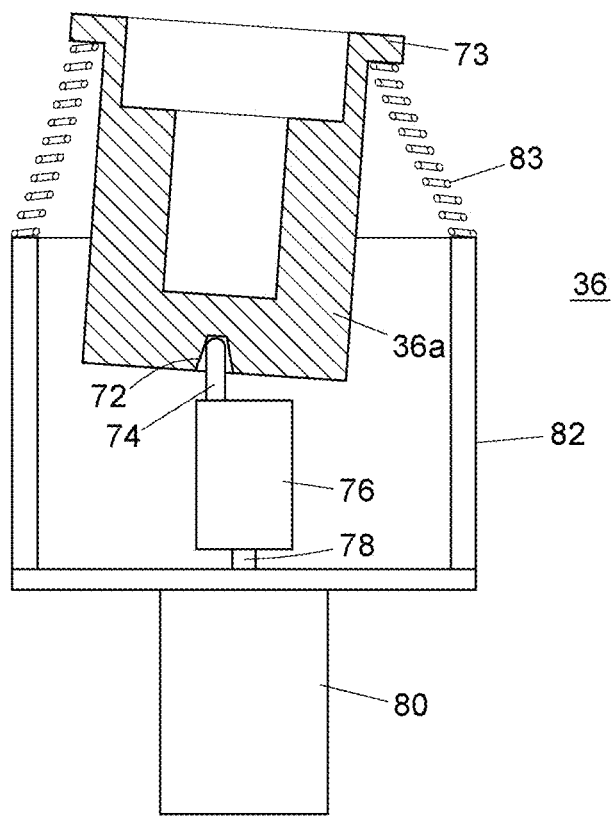
FIG. 6A is a cross-sectional configuration diagram showing a structure of a stirring part.
Figure 6B:
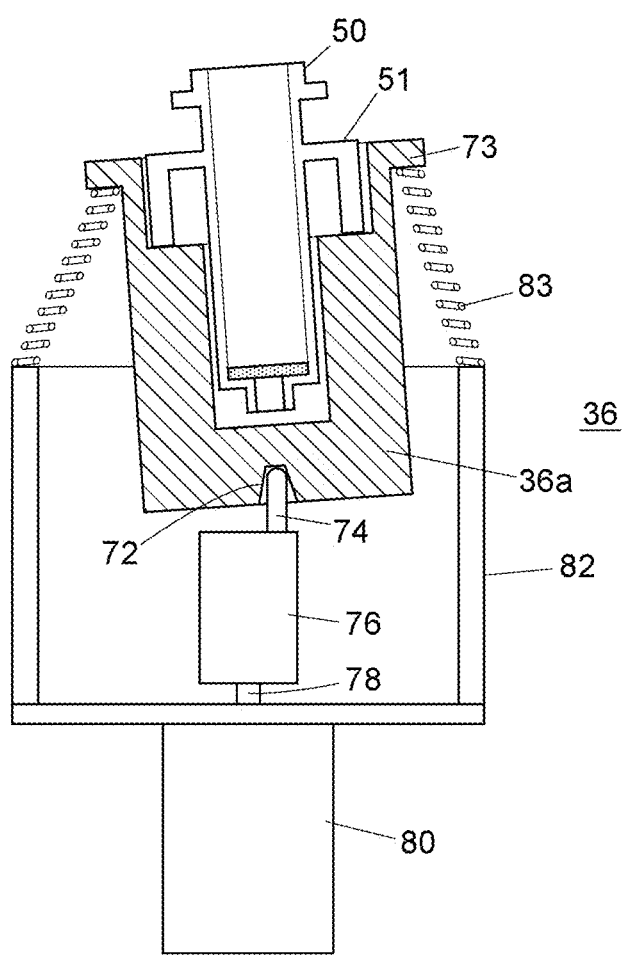
FIG. 6B is a cross-sectional configuration diagram showing an operation state of a stirring part.

Next, a structure of the stirring part 36 will be described with reference to FIGS. 6A and 6B. FIGS. 6A and 6B show one stirring port 36a of the stirring part 36.

The stirring port 36a of the stirring part 36 is a container which contains the separation device 50. The stirring port 36a is driven by a stirring mechanism provided below the stirring port 36a.

The stirring mechanism which drives the stirring port 36a will be described. A rotor 76 is placed below the stirring port 36a, and a driving shaft 74 which is vertically placed is attached in a position displaced with respect to a center of an upper surface of the rotor 76. An upper end of the driving shaft 74 is inserted into a supporting hole 72 provided in a lower surface of the stirring port 36a. The rotor 76 is supported by a rotation shaft 78 rotated by a motor 80, and driving of the motor 80 causes rotation of the rotor 76, which is followed by revolving of the driving shaft 74 in a horizontal plane.

A supporting flame 82 is attached to the motor 80. The supporting flame 82 includes a sidewall extending vertically upward from the motor 80 side, and one end of an elastic member 83 such as a coil spring is attached to an upper end of the sidewall. The other end of the elastic member 83 is attached to an outer surface of an upper portion of the stirring port 36a, and elastically holds the upper portion of the stirring port 36a. The elastic member 83 is provided in each of plural positions (four positions, for example) which are evenly spaced from each other and surround the stirring port 36a.

When the motor 80 is driven with the separation device 50 containing a sample and a reagent being contained in the stirring port 36a, the driving shaft 74 revolves in a horizontal plane, which is followed by revolving of a lower end of a collecting container 72, as shown in FIG. 6B. This causes stirring in the separation device 50 contained in the stirring port 36a, so that a sample and a reagent are mixed.

Referring back to FIG. 1, the preprocessing apparatus 1 includes a sample transfer apparatus 42 for transferring a sample which is extracted to be in the collecting container 54, to a sample injecting apparatus (such as an automatic sampler, for example) placed adjacent to the preprocessing apparatus 1, at a lateral edge on a casing side. The sample transfer apparatus 42 includes a moving part 44 which is caused to move along one line (as indicated by arrows in FIG. 1) in a horizontal plane by a driving mechanism including a rack-and-pinion mechanism. A transfer port 43 for setting the collecting container 54 containing an extracted sample is provided in an upper surface of the moving part 44.

While no sample is transferred to the sample injecting apparatus, the transfer port 43 is placed in a position along a track of the holding part 25 of the carrying arm 24 (a position indicated by a solid line in FIG. 1), and setting of the collecting container 54 in the transfer port 43 by the carrying arm 24, as well as retrieval of the collecting container 54 from the transfer port 43, is performed in this position.

In order to transfer a sample to the sample injecting apparatus, after the collecting container 54 containing an extracted sample is placed in the transfer port 43, the moving part 44 moves toward an outside of the preprocessing apparatus 1, and the transfer port 43 is placed in a position on a side where the adjacent sample injecting apparatus is provided (a position indicated by a broken line in FIG. 1). In this position, a nozzle for sampling which is provided in the sample injecting apparatus sucks a sample in the collecting container 54. When the sample injecting apparatus finishes sucking the sample, the moving part 44 returns to an original position (a position indicated by a solid line in FIG. 1), and the carrying arm 24 retrieves the collecting container 54. The collecting container 54 which is once used is carried to a disposal port 34 by the carrying arm 24, and is disposed of.

The preprocessing apparatus 1 includes the disposal port 34 for disposing of the separation device 50 and the collecting container 54 which are once used, in a position along a track of the holding part 25 of the carrying arm 24 near the dispensation port 32. Further, the preprocessing apparatus 1 includes a cleaning port 45 for cleaning the sampling nozzle 20*a* in a position along a track of the sampling nozzle 20*a*. Though not shown in the drawings, a cleaning port for cleaning the reagent nozzle 26*a* is provided in a position along a track of the reagent nozzle 26*a*.

Figure 7:
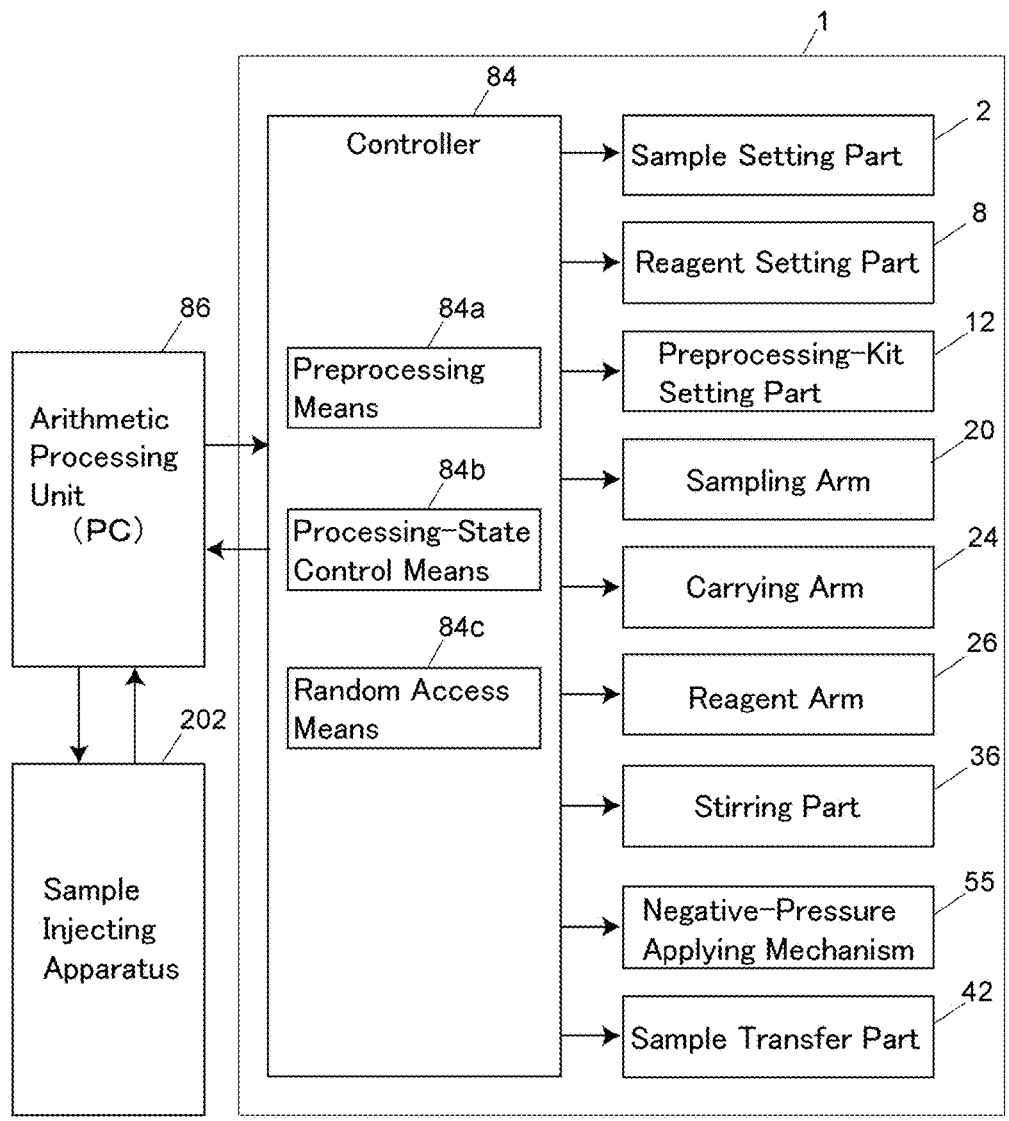
FIG. 7 is a block diagram showing a control system according to the embodiment.

Next, a control system of the preprocessing apparatus 1 will be described with reference to FIG. 7. In the following description, the term "port" means any ports including the filtration port 30, the dispensation port 32, the stirring port 36*a*, the temperature adjustment ports 38 and 40, and the transfer port 43, in each of which the separation device 50 or the collecting container 54 is to be set.

A controller 84 controls operations of the sample setting part 2, the reagent setting part 8, the preprocessing-kit setting part 12, the sampling arm 20, the carrying arm 24, the reagent arm 26, the stirring part 36, the sample transfer apparatus 42, and the negative-pressure applying mechanism 55 which are included in the preprocessing apparatus 1. The controller 84 is implemented by a computer provided in the preprocessing apparatus 1 and software executed by the computer. The controller 84 is connected with an arithmetic processing unit 86 implemented by a personal computer (PC) or a dedicated computer, for example, and an analyst controls the preprocessing apparatus 1 via the arithmetic processing unit 86. The arithmetic processing unit 86 is electrically connected with a liquid chromatograph system (which will be hereinafter referred to as an "LC system") 200 (refer to FIGS. 13 and 14) which is placed adjacent to the preprocessing apparatus 1 and analyzes a sample which has been subjected to preprocessing in the preprocessing apparatus 1, and a sample injecting apparatus 202 included in the LC system 200 operates in association with the preprocessing apparatus 1. FIG. 7 shows only the sample injecting apparatus 202 in the LC system 200.

The controller 84 includes a preprocessing means 84*a*, a processing-state control means 84*b*, and a random access means 84*c*. Each of those means is a function fulfilled by execution of software in a computer forming the controller 84. As described above, a plurality of sample containers are set in the sample setting part 2, and samples contained in those sample containers are sequentially dispensed to the separation devices 50, and carried to ports respectively corresponding to preprocessing items which should be executed on the samples, respectively.

The random access means 84*c* is configured to confirm a processing item which should be next executed on each sample, check availability of a port corresponding to the confirmed processing item, and carry the separation device 50 or the collecting container 54 containing the sample to a port if the port is available. Further, in a case where there is no available port corresponding to the confirmed processing item, the separation device 50 or the collecting container 54 being processed is carried to the port as soon as a port becomes available. The random access means 84*c* is configured to check a processing state in each port, and control the carrying arm 24 in such away that the carrying arm 24 carries the separation device 50 which had been subjected to processing in a port, to another port where next processing is to be performed.

The processing-state control means 84*b* is configured to control availability of each port and a processing state in each port. Availability of each port can be controlled by remembering which of the ports is used for setting the separation device 50 or the collecting container 54. Further, a sensor which senses whether or not the separation device 50 or the collecting container 54 is set may be provided in each port so that availability of each port can be controlled based on a signal provided from the sensor. A processing state in each port can be controlled by checking whether or not a time required to perform processing in a certain port elapses from setting of the separation device 50 or the collecting container 54 in the certain port. A state of processing in the transfer port 43 (suction of a sample by the sample injecting apparatus 202) may be controlled by checking whether or not a signal indicating that suction of a sample is finished is received from the sample injecting apparatus 202.

Each of the ports is configured to perform predetermined processing in the port when the separation device 50 or the collecting container 54 is set in the port.

It is noted that while two filtration ports 30, three stirring ports 36*a*, and four temperature adjustment ports 38 or 40 are provided, priorities are assigned to the ports which are provided to perform the same processing, and the random access means 84*c* is configured to use those ports in descending order of priority. For example, in a case where both of the two filtration ports 30 are available in filtering a sample, the collecting container 54 is set in one of the two filtration ports 30 which has a higher priority, and the separation device 50 is set on the collecting container 54.

Figure 8:
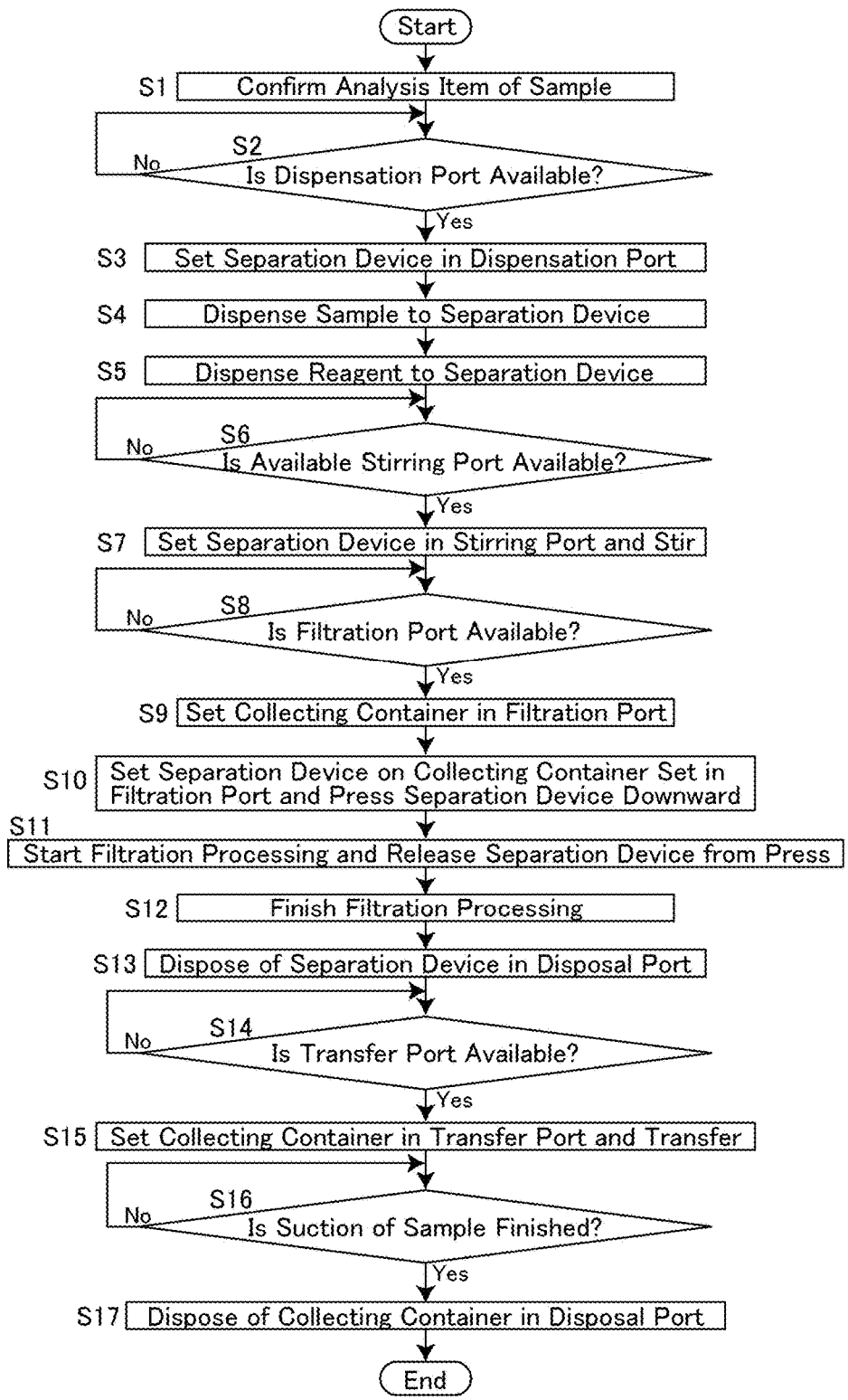
FIG. 8 is a flow chart showing an example of operations for preprocessing according to the embodiment.

An example of operations for preprocessing performed on one sample according to this embodiment will be described with reference to a flow chart of FIG. 8 together with FIG. 1. The flow chart of FIG. 8 shows only a flow of operations for preprocessing performed on one sample, and the operations for preprocessing are performed in parallel with and concurrently with, but independently of, operations for preprocessing performed on another sample. "To perform operations for preprocessing in parallel and concurrently, but independently" means that while filtration processing or stirring processing is performed on a certain sample in the filtration port 30 or the stirring port 36*a*, the carrying arm 24 carries the separation device 50 or the collecting container 54 containing a different sample to another port, where processing is performed on the different sample independently.

First, an analysis item which is previously designated by an analyst for a sample is confirmed (step S1), and a preprocessing item necessary for executing the confirmed analysis item is determined. It is checked whether or not the dispensation port 32 is available. If the dispensation port 32 is available, the carrying arm 24 takes out the separation device 50 being unused in which the sample is to be contained, from the preprocessing-kit setting part 12, and sets the separation device 50 in the dispensation port 32 (steps S2 and S3). Though the separation device 50 and the collecting container 54 are set in the preprocessing-kit setting part 12 with the separation device 50 and the collecting container 54 being stacked (in a state shown in FIG. 2C), the carrying arm 24 holds only the separation device 50 being on the collecting container 54 with the use of the holding part 25, and carries the separation device 50 to the dispensation port 32.

The sampling nozzle 20a dispenses the sample to the separation device 50 (step S4). After dispensing the sample to the separation device 50, the sampling nozzle 20a is cleaned in the cleaning port 45, and gets ready for dispensation of a next sample. The reagent dispensation nozzle 26a takes a reagent related to preprocessing which should be performed on the sample dispensed to the separation device 50, from the reagent container 10, and dispenses the reagent to the separation device 50 in the dispensation port 32 (step S5). Additionally, dispensation of a reagent to the separation device 50 may be performed before dispensation of the sample. Further, a reagent dispensation port for dispensing a reagent may be provided in a different position from that of the dispensation port 32 so that the carrying arm 24 can set the separation device 50 in the reagent dispensation port, for dispensation of a reagent in the different position.

After the sample and the reagent are dispensed to the separation device 50, availability of the stirring port 36a is checked (step S6). If the stirring port 36a is available, the carrying arm 24 shifts the separation device 50 from the dispensation port 32 to the available stirring port 36a, and stirring is performed (step S7). This stirring processing is performed for a certain period of time which is previously determined, so that the sample and the reagent in the separation device 50 are mixed. During this stirring processing, availability of the filtration port 30 is checked (step S8), and the carrying arm 24 sets the collecting container 54 in the filtration port 30 if the filtration port 30 is available (step S9). The collecting container 54 set in the filtration port 30 is the collecting container 54 which is paired with the separation device 50 in which stirring is being performed in the stirring port 36a, and is the collecting container 54 set in the preprocessing-kit setting part 12 with the separation device 50 in which stirring is being performed, being stacked thereon. Additionally, during this stirring processing, the carrying arm 24 can carry the separation device 50 or the collecting container 54 for another sample.

After stirring processing in the stirring part 36 is finished, the carrying arm 24 carries the separation device 50 to the filtration port 30, and sets the separation device 50 on the collecting container 54 so that a lower portion of the separation device 50 is contained in the collecting container 54 set in the filtration port 30 (a state shown in FIG. 4B, step S10). At that time, the separation device 50 is pressed downward (toward the filtration port 30), so that a lower end of the skirt part 51 of the separation device 50 is caused to descend to a level which is slightly (by approximately 0.1 mm) lower than a level of an upper surface of the sealing member 60 which is provided around the filtration port 30. As a result of this, a lower end of the skirt part 51 of the separation device 50 compresses the sealing member 60, which improves hermeticity between a lower end of the skirt part 51 and the sealing member 60. The carrying arm 24 keeps pressing the separation device 50 downward until a negative pressure is maintained in the filtration port 30 after a start of filtration processing described below.

While the filtration port 30 is hermetically sealed with the separation device 50 being set on the collecting container 54 in filtration port 30, filtration processing is started. In the filtration processing, the filtration port 30 is decompressed by the negative-pressure applying mechanism 55 so that a negative pressure is maintained in the filtration port 30 which contains the separation device 50 and the collecting container 54. As a result of the separation device 50 and the collecting container 54 being maintained for a certain period of time in the filtration port 30 which is under a negative pressure, a sample in the separation device 50 is filtered and extracted to be in the collecting container 54 (step S11).

When the pressure sensor 62 (refer to FIG. 5) senses that a pressure in the filtration port 30 becomes negative after filtration processing is started, the carrying arm 24 releases the separation device 50 from a downward press and a hold. After releasing the separation device 50 from a hold, the carrying arm 24 can carry another separation device 50 or another collecting container 54. Release of the separation device 50 from a downward press and a hold of the carrying arm 24 is not necessarily performed based on a sensing signal of the pressure sensor 62, and may be performed after a predetermined period of time elapses from a start of filtration processing.

Additionally, though not incorporated in the above-described operations for preprocessing, a temperature treatment in which a sample in the separation device 50 is maintained at a predetermined temperature for a certain period of time after the sample is stirred in the separation device 50, may be incorporated in some cases. In such a case, after stirring processing is finished, availability of the temperature adjustment port 40 is checked, and the separation device 50 is set in the temperature adjustment port 38 if the temperature adjustment port 38 is available. Then, after a certain period of time elapses, the separation device 50 is shifted from the temperature adjustment port 38, to be set on the collecting container 54 in the filtration port 30.

After filtration processing of the sample is finished (step S12), the three-way valve 64 (refer to FIG. 5) is switched so that an atmospheric pressure is maintained in the filtration port 30, and the holding part 25 of the carrying arm 24 takes out the separation device 50 which is used, from the filtration port 30, and disposes of the separation device 50 in the disposal port 34 (step S13).

Thereafter, availability of the transfer port 43 is checked (step S14). If the transfer port 43 is available, the carrying arm 24 carries the collecting container 54 in the filtration port 30 to the transfer apparatus 42, and sets the collecting container 54 in the transfer port 43. When the collecting container 54 is set in the transfer port 43, the moving part 44 is caused to move to a position (indicated by a broken line in FIG. 1) on a side where the sample injecting apparatus 202 included in the adjacently-placed LC system 200 (refer to FIGS. 13 and 14) is provided, so that the collecting container 54 is transferred to a side where the sample sucking apparatus 90 is provided (step S15). On a side where the sample injecting apparatus 202 is provided, a sampling nozzle sucks the sample in the collecting container 54 transferred by the transfer apparatus 42 (step S16). The moving part 44 stops at a position on a side where the LC system 200 is provided until the sample injecting apparatus 202 finishes sucking the sample, and the moving part 44 returns to an original position (indicated by a solid line in FIG. 1) when a signal indicating that suction of the sample is finished is received from the LC system 200.

After transfer of the sample is finished, the carrying arm 24 retrieves the collecting container 54 which is used, from the transfer port 43, and disposes of the collecting container 54 in the disposal port 34 (step S17).

Additionally, after filtration processing of the sample is finished, a temperature treatment in which the sample which is extracted to be in the collecting container 54 is maintained at a predetermined temperature for a certain period of time is performed, in some cases. In such a case, availability of the temperature adjustment port 40 is checked, and the collecting container 54 is set in the temperature adjustment port 40 if the temperature adjustment port 40 is available. Then, after a certain period of time elapses, the collecting container 54 is shifted from the temperature adjustment port 40 to the transfer port 43, where the sample is transferred.

Figure 9:
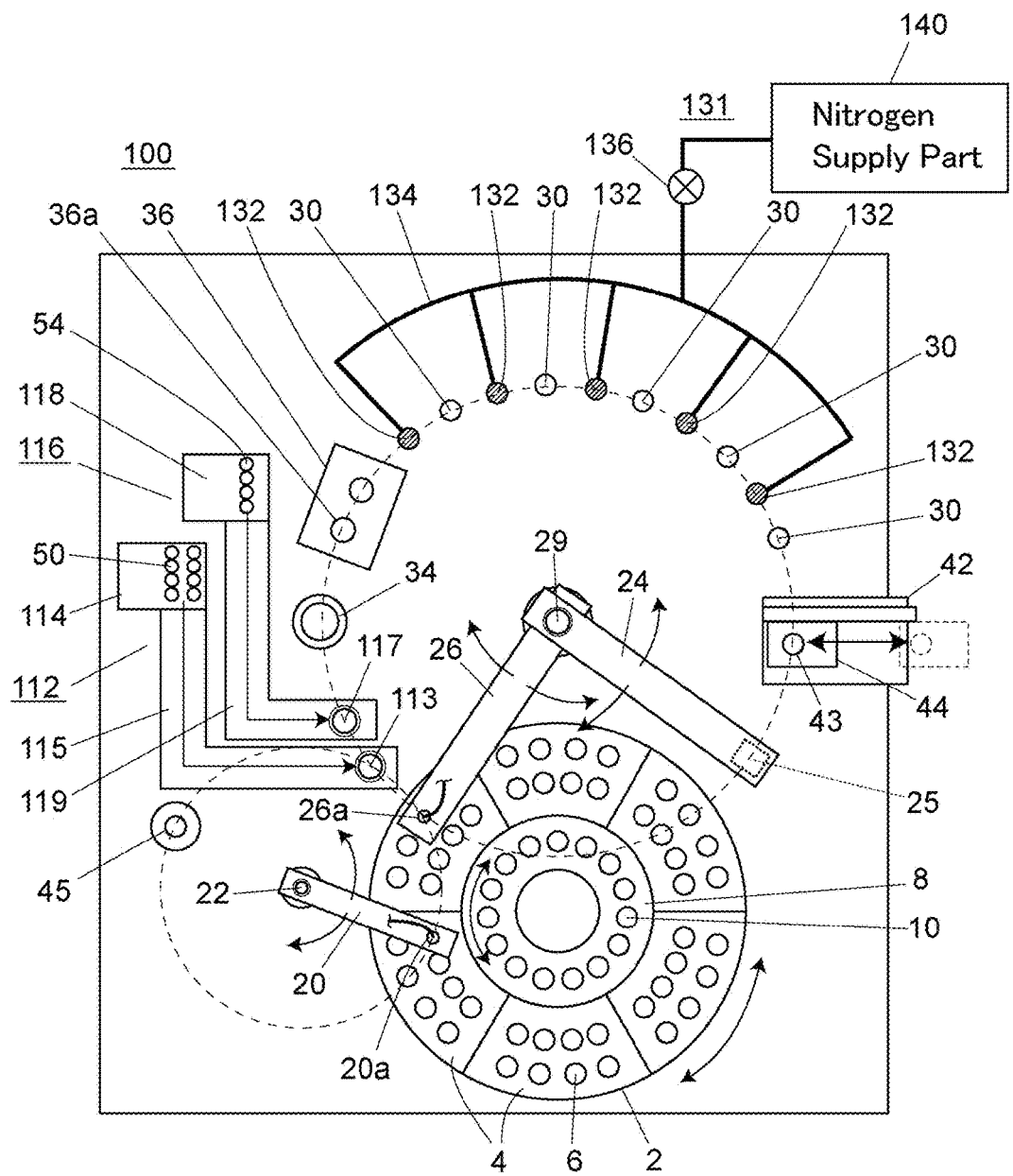
FIG. 9 is a plan view showing a different embodiment of a preprocessing apparatus.

Another embodiment of a preprocessing apparatus will be described with reference to FIG. 9. It is noted that in FIG. 9, the same structures as in FIG. 1 are denoted by the same reference symbols, and description about such the structures will be omitted in the following.

A preprocessing apparatus 100 includes a separation-device supply part 112 and a collecting-container supply part 116 as preprocessing-kit setting parts.

The separation-device supply part 112 automatically sets the separation device 50 in a separation-device setting port 113 which is provided in a position along a track of the holding part 25 of the carrying arm 24 and along a track of the sampling nozzle 20a of the sampling arm 20. The separation-device supply part 112 includes a separation-device holding part 114 in which a plurality of separation devices 50 being unused are held. The separation-device holding part 114 is placed at a higher level than the separation-device setting port 113, and includes a slope 115 which is inclined so as to descend from the separation-device holding part 114 to the separation-device setting port 113, between the separation-device holding part 114 and the separation-device setting port 113. When one of the separation devices 50 which are held by the separation-device holding part 114 is released from a hold, the released separation device 50 slides on the slope 115 due to a gravity, and is set in the separation-device setting port 113.

The collecting-container supply part 116 automatically sets the collecting container 54 in a collecting-container setting port 117 which is provided in a position along a track of the holding part 25 of the carrying arm 24. The collecting-container supply part 116 includes a collecting-container holding part 118 in which a plurality of collecting containers 54 being unused are held. The collecting-container holding part 118 is placed at a higher level than the collecting-container setting port 117, and includes a slope 119 which is inclined so as to descend from the collecting-container holding part 118 to the collecting-container setting port 117, between the collecting-container holding part 118 and the collecting-container setting port 117. When one of the collecting containers 54 which are held by the collecting-container holding part 118 is released from a hold, the released collecting container 54 slides on the slope 119 due to a gravity, and is set in the collecting-container setting port 117.

According to this embodiment, the filtration ports 30 are provided in plural positions along a track of the holding part 25 of the carrying arm 24, and further, drying/solidifying-gas supply nozzles 132 are placed in respective positions near the filtration ports 30 and along a track of the holding part 25 of the carrying arm 24. The drying/solidifying-gas supply nozzles 132 form a part of a drying/solidifying mechanism 131 which blows a nitrogen gas as a drying/solidifying gas to a sample which is extracted to be in the collecting container 54 in the filtration port 30, to dry and solidify the sample. A nitrogen gas is supplied to each of the drying/solidifying-gas supply nozzles 132 from a nitrogen supply part 140 through a drying/solidifying-gas supply path 134 as needed. A flow rate of nitrogen gas supplied from the nitrogen supply part 140 is controlled by a valve 136.

Figure 10A:
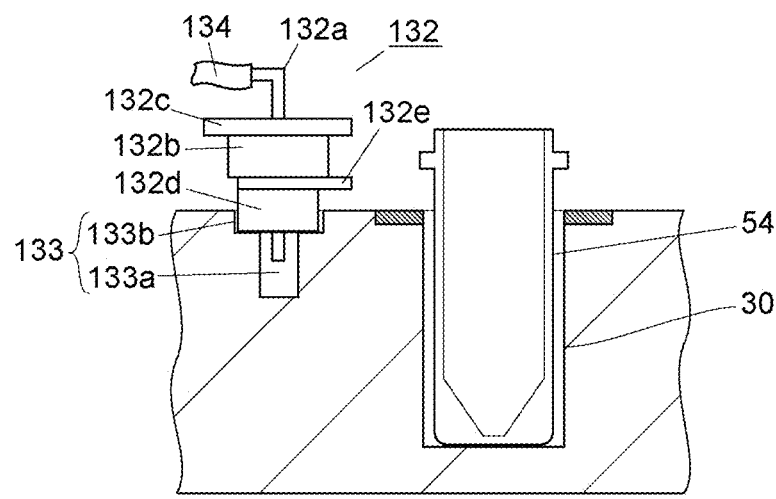
FIG. 10A is a cross-sectional configuration diagram showing a part of a drying/solidifying mechanism together with a filtration port.

An example of the drying/solidifying-gas supply nozzle 132 will be described with reference to FIGS. 10A and 10B. It is noted that while FIGS. 10A and 10B show the filtration port 30 in a simplified manner, the filtration port 30 may be of a type which has the same structure as shown in FIGS. 4A to 4D.

A nozzle setting port 133 is provided near each of the filtration ports 30. The nozzle setting port 133 includes a hole 133a into which a tip of the drying/solidifying-gas supply nozzle 132 of the drying/solidifying mechanism 131 is inserted, and a depression 133b provided at an edge of the hole 133a. The drying/solidifying-gas supply nozzle 132 includes a tip-side body 132d which has a shape fitted into the depression 133b, on a tip side, and as a result of the tip-side body 132d being fitted into the depression 133b, the drying/solidifying-gas supply nozzle 132 is set with a nozzle tip being oriented vertically downward in the nozzle setting port 133.

The drying/solidifying-gas supply nozzle 132 includes: a first flange part 132c which is engaged with the finger parts 46 (refer to FIG. 3) of the holding part 25 of the carrying arm 24, on a base-end side in a pipe 132a to which a tube forming the drying/solidifying-gas supply path 134 is attached; a base-side body 132b in a position closer to a nozzle tip than the flange part 132c; and a second flange part 132e in a position more closer to a nozzle tip. The holding part 25 of the carrying arm 24 carries the drying/solidifying-gas supply nozzle 132 by holding the first flange part 132c with the finger parts 46.

Figure 10B:
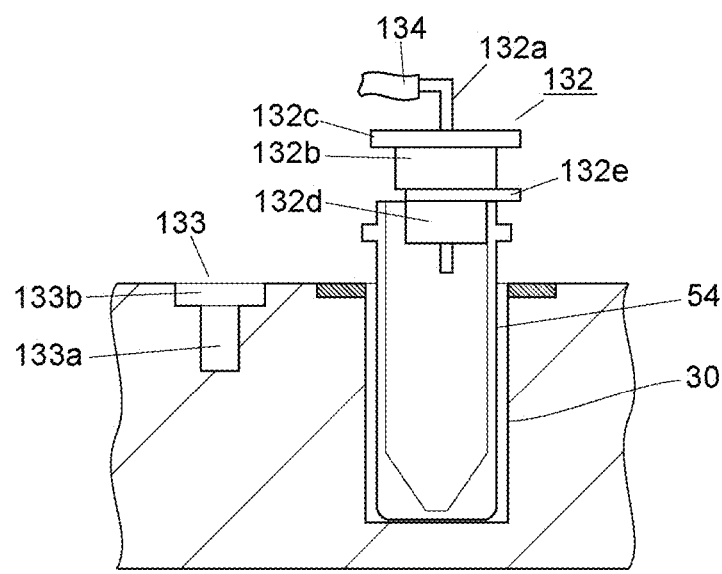
FIG. 10B is a cross-sectional view showing a state where a drying/solidifying-gas supply nozzle is placed on a collecting container.

In order to dry and solidify a sample in the collecting container 54, as shown in FIG. 10B, the carrying arm 24 sets the drying/solidifying-gas supply nozzle 132 in an opening in an upper surface of the collecting container 54, and a nitrogen gas is vertically blown to the sample in the collecting container 54. As a result of the drying/solidifying-gas supply nozzle 132 being set in the opening in the upper surface of the collecting container 54, the second flange part 132e of the drying/solidifying-gas supply nozzle 132 comes into contact with an edge of the opening of the collecting container 54, so that the base-side body 132b and the first flange part 132c of the drying/solidifying-gas supply nozzle 132 can be kept exposed above the collecting container 54. Consequently, after drying/solidifying processing is finished, the holding part 25 of the carrying arm 24 can hold the drying/solidifying-gas supply nozzle 132, and put the drying/solidifying-gas supply nozzle 132 back to the nozzle setting port 133.

The drying/solidifying-gas supply nozzle 132 blows a nitrogen gas to the extracted sample which is provided from the separation device 50, to achieve concentration or drying/solidifying, (hereinafter, either will be referred to as "drying/solidifying processing") of the sample. In performing drying/solidifying processing, as shown in FIG. 10B, the carrying arm 24 carries the drying/solidifying-gas supply nozzle 132 to a position above the collecting container 54 so that the flange part 132e of the drying/solidifying-gas supply nozzle 132 comes into contact with the edge of the upper surface of the collecting container 54. Accordingly, a tip of the drying/solidifying-gas supply nozzle 132 is kept oriented vertically downward without having the drying/solidifying-gas supply nozzle 132 held by the carrying arm 24. Drying/solidifying processing is performed on a sample in such a state, and during this drying/solidifying processing, the carrying arm 24 can perform another processing.

Figure 11:
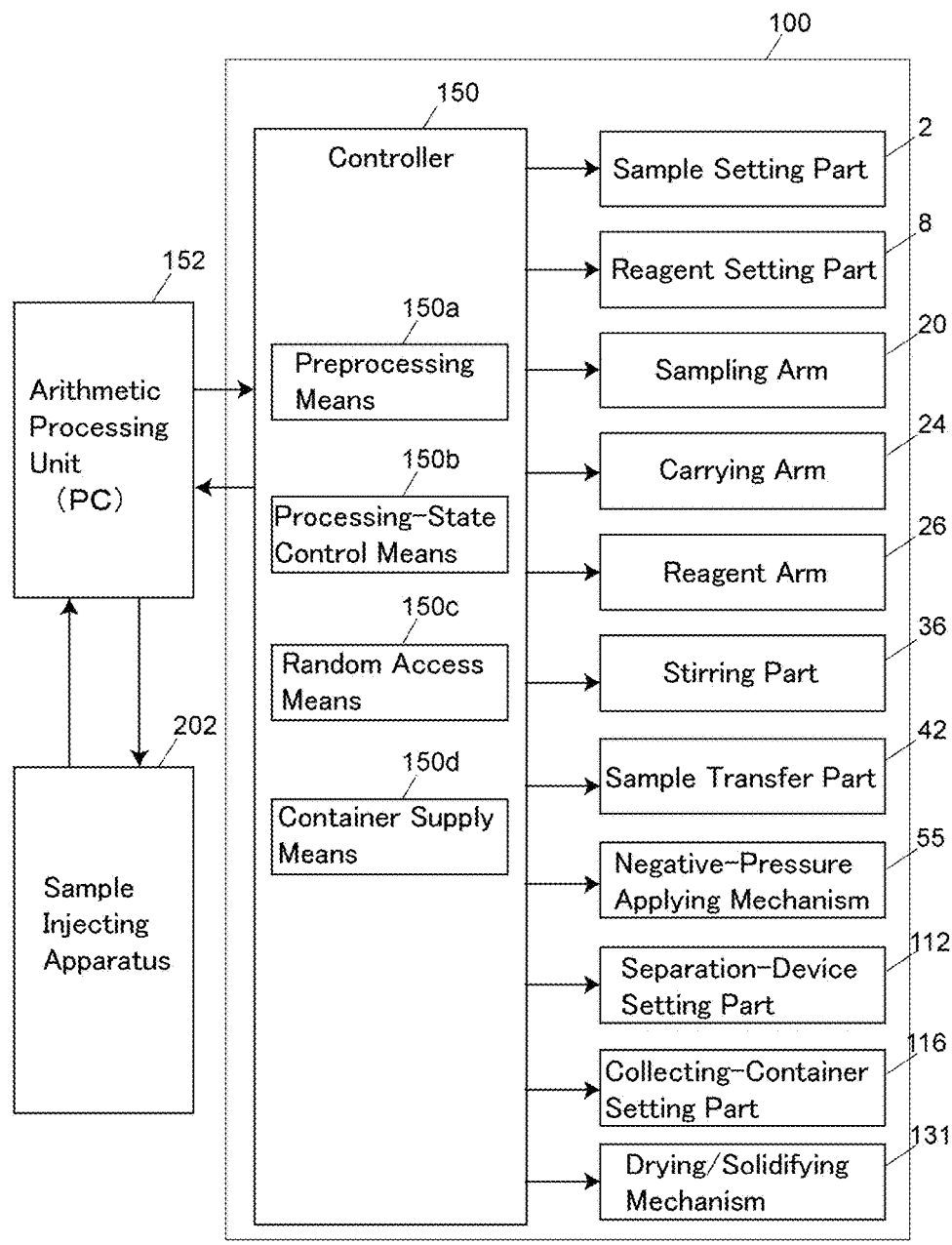
FIG. 11 is a block diagram showing a control system according to the different embodiment.

FIG. 11 shows a control system according to this embodiment.

A controller 150 controls operations of the separation-device supply part 112, the collecting-container supply part 116, and the drying/solidifying mechanism 131, as well as operations of the sample setting part 2, the reagent setting part 8, the preprocessing-kit setting part 12, the sampling arm 20, the carrying arm 24, the reagent arm 26, the stirring part 36, the sample transfer apparatus 42, and the negative-pressure applying mechanism 55. The controller 150 is implemented by a computer provided in the preprocessing apparatus 100 and software executed by the computer. The controller 150 is connected with an arithmetic processing unit 152 implemented by a personal computer (PC) or a dedicated computer, for example, and an analyst controls the preprocessing apparatus 100 via the arithmetic processing unit 152. The arithmetic processing unit 152 is connected with the sample injecting apparatus 202.

The controller 150 includes a preprocessing means 150a, a processing-state control means 150b, a random access means 150c, and a container supply means 150d. Each of those means is a function fulfilled by execution of software in a computer forming the controller 150. The preprocessing means 150a, the processing-state control means 150b, and the random access means 150c have the same functions as the preprocessing means 84a, the processing-state control means 84b, and the random access means 84c in FIG. 7, respectively. The container supply means 150d is configured to control the separation-device supply part 112 and the collecting-container supply part 116 in such a way that the separation device 50 is set in the separation-device setting port 113 and the collecting container 54 is set in the collecting-container setting port 117 at appropriate points in time.

Figure 12:
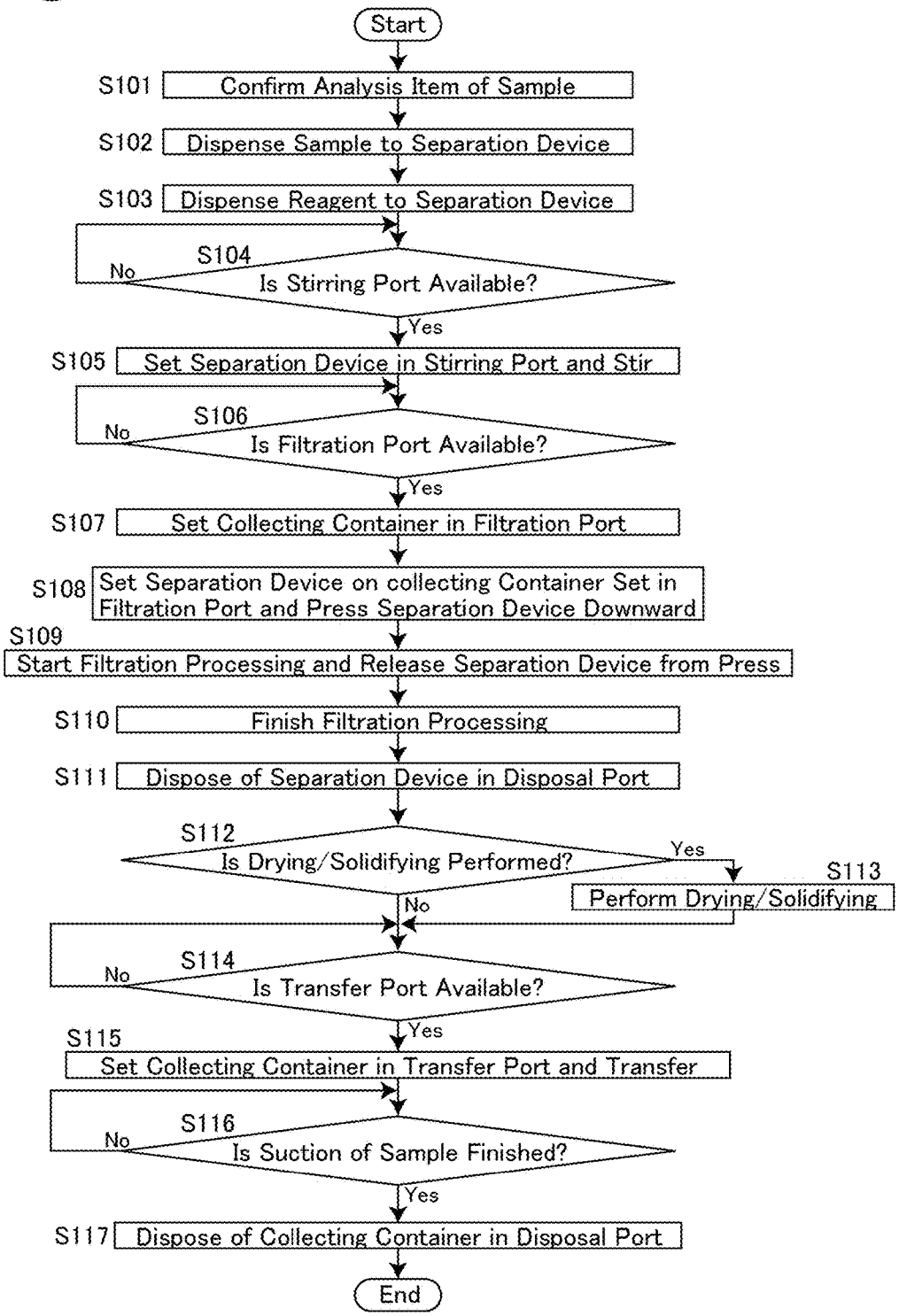
FIG. 12 is a flow chart showing an example of operations for preprocessing according to the different embodiment.

An example of operations for preprocessing performed on one sample according to this embodiment will be described with reference to a flow chart of FIG. 12 together with FIG. 9. The flow chart of FIG. 12, in the same way as the flow chart of FIG. 8, shows only a flow of operations for preprocessing preformed on one sample, and the operations for preprocessing are performed in parallel with and concurrently with, but independently of, operations for preprocessing performed on another sample.

First, an analysis item which is previously designated by an analyst for a sample is confirmed (step 101), and a preprocessing item necessary for executing the confirmed analysis item is determined. The separation-device supply part 112 sets the separation device 50 being unused in the separation-device setting port 113, and the sampling nozzle 20a dispenses the sample to the set separation device 50 (step S102). After dispensing the sample to the separation device 50, the sampling nozzle 20a is cleaned in the cleaning port 45, and gets ready for dispensation of a next sample. The reagent dispensation nozzle 26a takes a reagent related to preprocessing which should be performed on the sample dispensed to the separation device 50, from the reagent container 10, and dispenses the reagent to the separation device 50 in the separation-device setting port 113 (step S103).

Additionally, dispensation of a reagent to the separation device 50 may be performed before dispensation of the sample. Further, the reagent dispensation port for dispensing a reagent may be provided in a different position so that the carrying arm 24 can set the separation device 50 in the reagent dispensation port, to achieve dispensation of a reagent in the different position.

After the sample and the reagent are dispensed to the separation device 50, availability of the stirring port 36a is checked (step S104). If the stirring port 36a is available, the carrying arm 24 shifts the separation device 50 from the separation-device setting port 113 to the available stirring port 36a, and stirring is performed (step S105). This stirring processing is performed for a certain period of time which is previously determined, so that the sample and the reagent in the separation device 50 are mixed. During this stirring processing, availability of the filtration port 30 is checked (step S106), and the carrying arm 24 carries the collecting container 54 which is unused and set in the collecting-container setting port 117, to the filtration port 30, and sets the collecting container 54 if the filtration port 30 is available (step S107). During this stirring processing, the carrying arm can carry the separation device 50 or the collecting container 54 for another sample.

After stirring processing in the stirring part 36 is finished, the carrying arm 24 sets the separation device 50 on the filtration port 30 so that a lower portion of the separation device 50 is contained in the collecting container 54 set in the filtration port 30, and presses the separation device 50 downward (step S108). With the separation device 50 being pressed downward by the carrying arm 24, the negative-pressure applying mechanism 55 decompresses the filtration port 30 so that a negative pressure is maintained in the filtration port 30 containing the separation device 50 and the collecting container 54 (step S109). As a result of the filtration port 30 being maintained under a negative pressure for a certain period of time, a sample in the separation device 50 is filtered and extracted to be in the collecting container 54. The carrying arm 24 releases the separation device 50 from a downward press and a hold when a negative pressure is maintained in the filtration port 30, or when a predetermined period of time elapses from a start of filtration processing. Thereafter, the carrying arm 24 can carry another separation device 50 or another collecting container 54.

After filtration processing of the sample is finished (step S110), the three-way valve 64 (refer to FIG. 5) is switched so that an atmospheric pressure is maintained in the filtration port 30, and the holding part 25 of the carrying arm 24 takes out the separation device 50 which is used, from the filtration port 30, and disposes of the separation device 50 in the disposal port 34 (step S111). Thereafter, in a case where the sample which is extracted to be in the collecting container 54 should be dried and solidified, the drying/solidifying-gas supply nozzle 132 is set in an opening in an upper surface of the collecting container 54, and drying/solidifying is performed (steps S112 and S113). During this drying/solidifying processing as well, the carrying arm 24 can carry the separation device 50 or the collecting container 54 for another sample.

After filtration processing of the sample is finished in a case where drying/solidifying of the sample is not performed, or after drying/solidifying of the sample is finished in a case where the sample should be dried and solidified, availability of the transfer port 43 is checked (step S114), and the carrying arm 24 carries the collecting container 54 in the filtration port 30 to the transfer apparatus 42 and sets the collecting container 54 in the transfer port 43 if the transfer port 43 is available (step S115). Operations for transfer of the sample and operations for disposal of the collecting container 54 which are to be performed thereafter are the same as the operations for preprocessing which have been described above with reference to the flow chart of FIG. 8 (step S116 and S117).

The above-described embodiments are mere examples of preferred embodiments of the present invention, and positions and the numbers of ports such as the filtration port 30, the stirring port 36a, the temperature adjustment ports 38 and 40, and the transfer port 43 can be appropriately changed as needed.

Figure 15A:
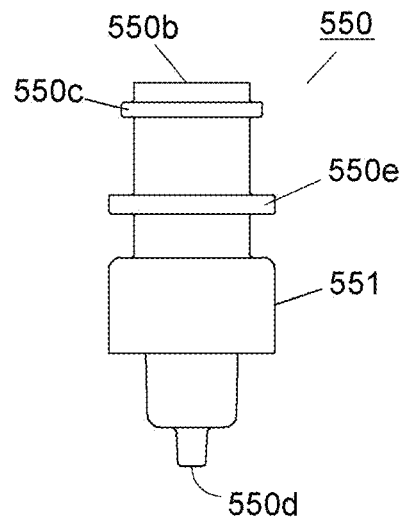
FIG. 15A is a front view showing another embodiment of a separation device of a preprocessing kit.
Figure 15B:
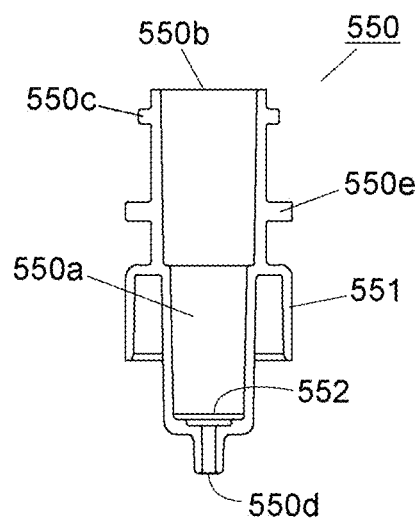
FIG. 15B is a cross-sectional view of the separation device.
Figure 16A:
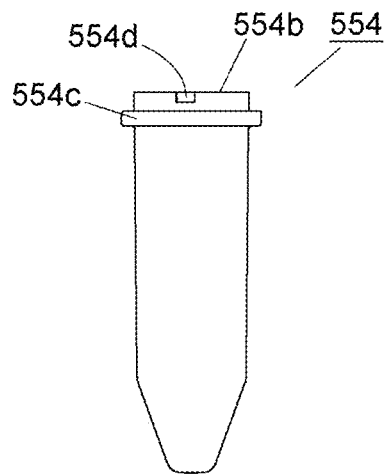
FIG. 16A is a front view showing another embodiment of a collecting container of a preprocessing kit.
Figure 16B:
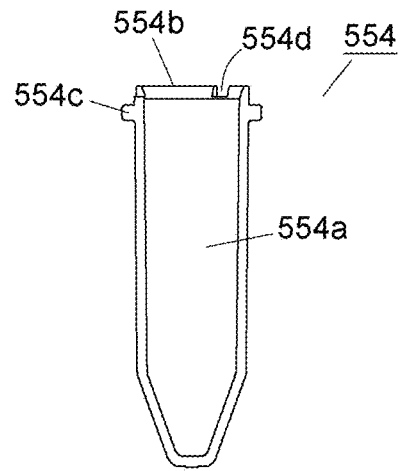
FIG. 16B is a cross-sectional view of the collecting container.

In the preprocessing apparatus 1 (or 100), a separation device 550 shown in FIGS. 15A and 15B and a collecting container 554 shown in FIGS. 16A and 16B can be used in place of the separation device 50 and the collecting container 54 shown in FIGS. 2A to 2D. Below, with regard to the separation device 550 and the collecting container 554, differences from the separation device 50 and the collecting container 54 will be described.

In the separation device 550 shown in FIGS. 15A and 15B, each of an inner diameter and an outer diameter of a portion located below a base portion of a skirt part 551 (a lower portion of the device) is smaller than that of a portion located above the portion. The lower portion of the device is contained in a space 554a of the collecting container 554. This can make an outer diameter of a portion where a flange part 550c of the separation device 550 is provided, identical to an outer diameter of a portion where a flange part 554c of the collecting container 554 is provided. Accordingly, respective shapes and respective dimensions of the flange part 550c of the separation device 550 and the flange part 554c of the collecting container 554 can exactly agree with each other, so that the holding part 25 of the carrying arm 24 can hold the separation device 550 and the collecting container 554 in a similar fashion.

A protruding part 550e which circumferentially protrudes in a shape of a flange like the flange part 550c is provided between the flange part 550c and a base portion of the skirt part 551 in an outer circumferential surface of the separation device 550. The protruding part 550e is provided in a position which corresponds to an upper end of an inner wall of the stirring port 36a when the separation device 550 is set in the stirring port 36a. The protruding part 550e has the same outer diameter as that of the skirt part 551, and comes into contact with an upper end of an inner wall of the stirring port 36a when stirring processing is performed, to prevent vibration of the separation device 550 in the stirring port 36a.

The collecting container 554 shown in FIGS. 16A and 16B includes notches 554d in plural positions (three positions, for example) at an edge of an upper-surface opening 554b. The notches 554d form openings for allowing circulation of air between an inner wall of a base portion of the skirt part 551 and an upper end of the collecting container 554 when the separation device 550 and the collecting container 554 are integrated with each other and an upper portion of the collecting container 554 enters into the skirt part 551 of the separation device 550. To achieve filtration processing in the filtration port 30, air in the filtration port 30 is sucked with the separation device 550 and the collecting container 554 which are integrated with each other being set in the filtration port 30, and a pressure in the collecting container 554 is made negative. At that time, air in the collecting container 554 passes through openings formed by the notches 554d, so that the collecting container 554 can be efficiently decompressed.

Figure 13:
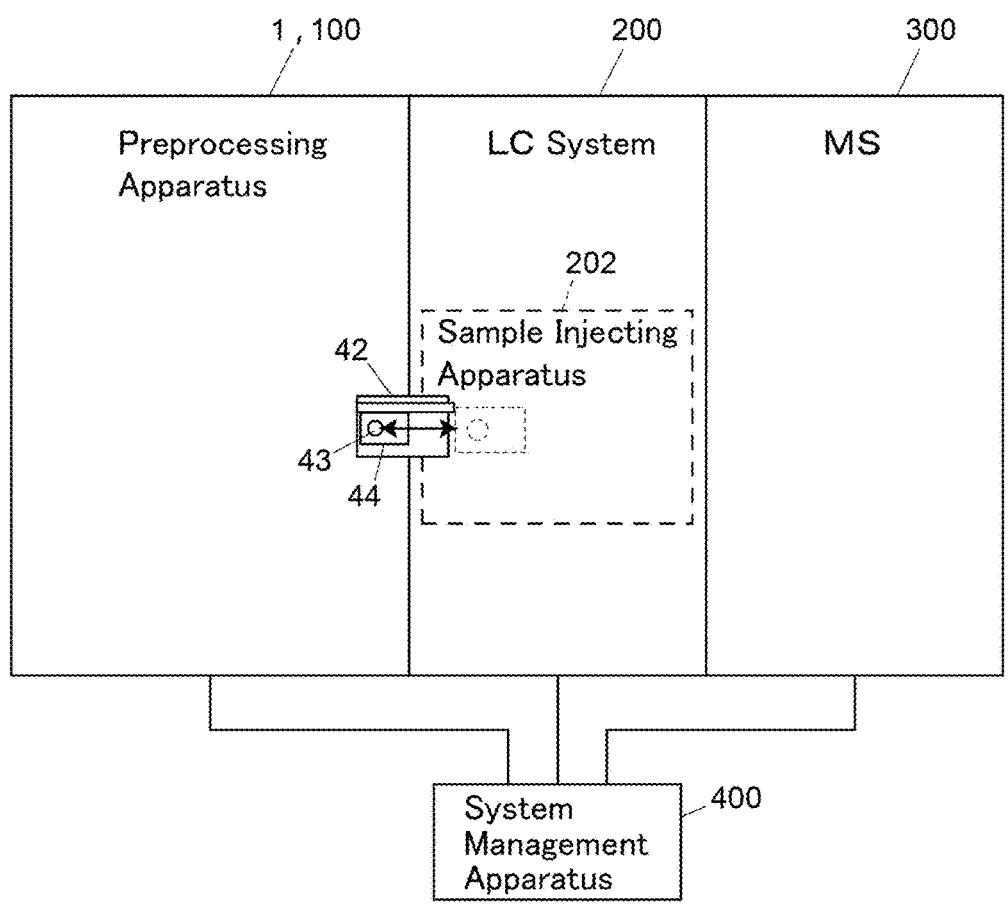
FIG. 13 is a block diagram schematically showing one embodiment of an analysis system.

Next, one embodiment of an analysis system including the preprocessing apparatus 1 (or 100) will be described with reference to FIG. 13.

The LC system 200 is placed adjacent to the preprocessing apparatus 1 (or 100) described above in the foregoing embodiment, and further, a mass spectrometer (MS) is placed adjacent to the LC system 200. Operations of the preprocessing apparatus 1 (or 100), the LC system 200, and the MS 300 are managed by a common system management apparatus 400. The system management apparatus 400 is a dedicated computer or a general-purpose PC which includes software for controlling and managing the preprocessing apparatus 1 (or 100), the LC system 200, and the MS 300, and includes also functions of the arithmetic processing unit 86 in FIG. 7 or the arithmetic processing unit 152 in FIG. 11.

The LC system 200 includes the sample injecting apparatus 202 which takes a sample which has been subjected to preprocessing in the preprocessing apparatus 1 (or 100), and injects the sample into an analytical flow path of a liquid chromatograph. As described above, the preprocessing apparatus 1 (or 100) includes the transfer apparatus 42 which transfers the collecting container 54 (or 554) containing the preprocessed sample to a side where the LC system 200 is provided, and the sample injecting apparatus 202 takes a sample from the collecting container 54 (or 554) which is transferred to aside where the LC system 200 is provided, by the transfer apparatus 42. When the moving part 44 of the transfer apparatus 42 moves to a side where the LC system 200 is provided, the collecting container 54 (or 554) set in the transfer port 43 of the moving part 44 is placed in a predetermined position in the sample injecting apparatus 202.

When the collecting container 54 (or 554) containing the sample which has been subjected to preprocessing in the preprocessing apparatus 1 (or 100) is set in the transfer port 43 of the transfer apparatus 42 and the moving part 44 moves to a side where the LC system 200 is provided so that the collecting container 54 (or 554) is placed in a predetermined position in the sample injecting apparatus 202, a signal to that effect is sent to the sample injecting apparatus 202 via the system management apparatus 400. Then, the sample injecting apparatus 202 starts operations for taking the sample from the collecting container 54 (or 554). The transfer apparatus 42 holds the collecting container 54 (or 554) in a predetermined position in the sample injecting apparatus 202 until the sample injecting apparatus 202 finishes taking the sample. After the sample injecting apparatus 202 finishes taking the sample, a signal to that effect is sent to the preprocessing apparatus 1 (or 100) via the system management apparatus 400. Then, the transfer apparatus 42 causes the moving part 44 to move to a side where the preprocessing apparatus 1 (or 100) is provided, and returns the collecting container 54 (or 554) to a predetermined position in the preprocessing apparatus 1 (or 100). The collecting container 54 (or 554) returned to a side where the preprocessing apparatus 1 (or 100) is provided is carried to the disposal port 34 by the carrying arm 24, and is disposed of.

The LC system 200 according to this embodiment will be described with reference to FIG. 14.

The LC system 200 includes a liquid delivery apparatus 204, a column oven 206, and a detector 208, in addition to the sample injecting apparatus 202. The liquid delivery apparatus 204 is an apparatus which delivers, for example, two kinds of solvents to a mixer with a liquid delivery pump, and delivers a solution resulted from mixture in the mixer as a mobile phase. The column oven 206 includes an analytical column 207 which separates a sample into individual components. The detector 208 is a detector such as an ultraviolet-ray absorption detector, which detects a sample component separated in the analytical column 207.

The liquid delivery apparatus 204 is located in an upstream end of an upstream analytical flow path 218, and delivers a mobile phase through the upstream analytical flow path 218. The analytical column 207 and the detector 208 are provided on a downstream analytical flow path 220. Both of the upstream analytical flow path 218 and the downstream analytical flow path 220 are connected to ports of a two-position valve 210 provided in the sample injecting apparatus 202, and are connected with each other via the two-position valve 210.

The two-position valve 210 of the sample injecting apparatus 202 includes six ports. The respective ports of the two-position valve 210 are connected with a sample introduction flow path 212, a drainage flow path 214, and one end and the other end of a sample loop 216, as well as the upstream analytical flow path 218 and the downstream analytical flow path 220. Those are configured in such a way that to switch the two-position valve 210 could select either a state (1) where the sample introduction flow path 212, the sample loop 216, and the drainage flow path 214 are connected in series, and the downstream analytical flow path 220 is connected immediately downstream of the upstream analytical flow path 218 (a state shown in FIG. 14), or a state (2) where the upstream analytical flow path 218, the sample loop 216, and the downstream analytical flow path 220 are connected in series. The sample introduction flow path 212 communicates with an injection port 213.

The sample injecting apparatus 202 includes a needle 222 which can inject and discharge a liquid from a tip thereof, and a syringe pump 226 connected with the needle 222 via a flow path. The needle 222 is caused to horizontally and vertically move by a driving mechanism not shown in the drawings, and can take a sample from the collecting container 54 (or 554) which is transferred to a side where the LC system 200 is provided, by the transfer apparatus 42, and inject the sample from the injection port 213. The syringe pump 226 is connected also with a cleaning-liquid container 228 in which a cleaning liquid is stored, depending on switching of a flow-path selection valve 230. By connecting the syringe pump 228 which sucks a cleaning liquid with the needle 222 and delivering the cleaning liquid from the syringe pump 226 with the needle 222 being connected with the injection port 213, it is possible to clean inner surfaces of a sample loop 224, the needle 222, and the sample introduction flow path 212.

In order to take a sample from the collecting container (or 554), a tip of the needle 22 is inserted into the collecting container 54 (or 554), the syringe pump 226 sucks the sample, and the sample is held by the sample loop 224 provided between the needle 222 and the syringe pump 226. The sample held by the sample loop 224 is injected from the injection port 213. When the sample is injected from the injection port 213, the two-position valve 210 is operated so as to bring about a state (1) where the sample introduction flow path 212, the sample loop 216, and the drainage flow path 214 are connected in series, and the sample injected from the injection port 213 is held by the sample loop 216. Thereafter, the two-position valve 210 is switched so as to bring about a state (2) where the upstream analytical flow path 218, the sample loop 216, and the downstream analytical flow path 220 are connected in series, so that the sample held by the sample loop 216 is guided to the analytical column 207 by a mobile phase delivered from the liquid delivery apparatus 204, and the sample is separated into individual components in the analytical column 207. The individual components separated in the analytical column 207 are detected by the detector 208, and thereafter, are introduced into the MS 300.

A signal obtained in the detector 208 or the MS 300 is fetched by the system management apparatus 400 (refer to FIG. 13), and arithmetic processing for quantitative analysis or composition analysis of individual components separated in the analytical column 207 is performed by software installed in the system management apparatus 400 and hardware such as a CPU which executes the software.

DESCRIPTION OF REFERENCE SIGNS 1, 100: Preprocessing apparatus
2: Sample setting part
4: Sample rack
6: Sample container
8: Reagent setting part
10: Reagent container
12: Preprocessing-kit setting part
20: Sampling arm
20a: Sampling nozzle
22, 29: Shaft
24: Carrying arm
25: Holding part
26: Reagent arm
26a: Reagent arm
30: Filtration port
31: Collecting-container holding member
32: Dispensation port
34: Disposal port
36: Stirring part
36a: Stirring port
38: Temperature adjustment port for separation device
40: Temperature adjustment port for collecting container
42: Transfer apparatus
43: Transfer port
44: Moving part
45: Cleaning port
50, 550: Separation device
50a, 550a: Internal space of separation device
50b, 550b: Opening of separation device
50c, 550c: Flange part of separation device
50d, 550d: Extraction outlet
550e: Protruding part
51, 551: Skirt part
52, 552: Separation layer
52a: Deproteinizing filter
52b: Prefilter
54, 554: Collecting container
54a, 554a: Internal space of collecting container
54b, 554b: Opening of collecting container
54c, 554c: Flange part of collecting container
554d: Notch
55: Pressure applying mechanism
56: Hole
57: Pipe
58: Vacuum pump
60: Sealing member
62, 68: Pressure sensor 64, 70: Three-way valve
72: Supporting hole
73: Upper end of Stirring port
74: Driving shaft
76: Rotor
78: Rotation shaft
80: Motor
82: Supporting flame
83: Elastic member
84, 150: Controller
84a, 150a: Preprocessing means
84b, 150b: Processing-state control means
84c, 150c: Random access means
86, 152: Arithmetic processing unit
112: Separation-device supply part
113: Separation-device setting port
114: Separation-device holding part
115, 119: Slope
116: Collecting-container supply part
118: Collecting-container holding part
131: Drying/solidifying mechanism
132: Drying/solidifying-gas supply nozzle
133: Nozzle setting port
134: Pipe for supplying nozzle
136: Valve for controlling flow rate of drying/solidifying gas
140: Nitrogen supply part
200: LC system
202: Sample injecting apparatus
204: Liquid delivery apparatus
206: Column oven
207: Analytical column
208: Detector
210: Two-position valve
212: Sample introduction flow path
213: Injection port
214: Drainage flow path
216, 224: Sample loop
218: Upstream analytical flow path
220: Downstream analytical flow path
222: Needle
226: Syringe pump
228: Cleaning-liquid container
230: Selection valve
300: MS
400: System management apparatus

The invention claimed is:

1. A preprocessing apparatus comprising:
a preprocessing kit comprising:
  a cylindrical separation device having an internal space which is upwardly open, the cylindrical separation device including a separation layer which allows a sample to penetrate and separates a specific component in the sample from the sample, in the internal space, and including an extraction outlet for extracting the sample penetrating the separation layer, in a lower end;
  a collecting container having an opening which is upwardly open, and is attachable to and detachable from the separation device by insertion of a lower portion of the separation device into the opening, the collecting container having an internal space in which the sample extracted to be provided from the extraction outlet of the separation device is collected, and the collecting container being fitted into a recess part forming a filtration port for performing extraction processing on a sample with the lower end of the separation device being contained in the internal space; and
  a skirt part which is integrated with the separation device and is provided so as to surround an outer circumferential surface of the separation device with a clearance being left from the outer circumferential surface so that a space having a closed upper side and an open lower side is formed between the outer circumferential surface of the separation device and the skirt part, the skirt part being provided in such a way that a lower end of the skirt part comes into intimate contact with a peripheral surface of an opening of the recess part when the collecting container containing the lower end of the separation device is fitted into the recess part;
a carrying mechanism which includes a holding part holding the separation device and/or collecting container of the preprocessing kit, and moves the holding part, to carry the separation device and/or the collecting container;
a filtration part having an inner diameter which is larger than an outer diameter of the collecting container, the filtration part including at least one filtration port which includes a recess part in which the collecting container containing a lower end of the separation device is contained with a clearance being left from an outer circumferential surface of the collecting container, in a position along a track of the holding part, and including a pressure applying part which causes a negative pressure to be maintained in the at least one filtration port where the preprocessing kit is set;
a dispensation port for setting the separation device to which a sample or a reagent is to be dispensed;
a stirring port which holds the separation device containing the sample or the reagent, and causes the separation device to periodically move in a horizontal plane so that stirring occurs in the separation device, wherein
the dispensation port and the stirring port are provided in positions along a circumferential track which is made by the holding part along with the rotations of the carrying arm; and
a controller which controls operations of the carrying mechanism and the pressure applying part, the controller including a preprocessing means which is configured to set the separation device containing a sample to be subjected to filtration processing and the collecting container for collecting an extracted sample provided from the separation device in the filtration port, and to perform extraction processing on a sample in the filtration port while causing a negative pressure to be maintained in the filtration port.

2. The preprocessing apparatus according to claim 1, further comprising
a collecting-container holding member which comes into contact with the outer circumferential surface of the collecting container to elastically deform in a direction perpendicular to the outer circumferential surface when the collecting container is fitted into the filtration port, and uniformly presses the outer circumferential surface of the collecting container from a periphery of the collecting container to hold the collecting container in a central portion of the filtration port, the collecting-container holding member being provided in an inner side surface of the filtration port.

3. The preprocessing apparatus according to claim 2, wherein
the collecting-container holding member includes plate springs provided in plural positions which are circumferentially arranged and evenly spaced from each other in the inner side surface of the at least one filtration port.

4. The preprocessing apparatus according to claim 1, further comprising
a sealing member formed of an elastic material which enhances adherence to a lower end of the skirt part of the preprocessing kit, in a portion which surrounds an opening of the recess part forming the at least one filtration port and comes into contact with the lower end of the skirt part.

5. The preprocessing apparatus according to claim 4, wherein the holding part of the carrying mechanism is configured to press the separation device after setting the separation device and the collecting container in the at least one filtration port.

6. The preprocessing apparatus according to claim 1, wherein the at least one filtration port includes a plurality of the filtration ports,
the pressure applying part is configured to make a pressure in each of the filtration ports, negative, and the controller is configured to control a state of filtration processing in the filtration ports and availability of each of the filtration ports; and a random access means which is configured to check availability of the filtration ports when a sample to be subjected to filtration processing is provided, and set the separation device containing the sample and the collecting container collecting an extract of the sample in an available filtration port when there is any available filtration port.

7. The preprocessing apparatus according to claim 1, wherein
the carrying mechanism is a carrying arm which horizontally extends, has a base end which is pivotally supported by a shaft extending vertically, and is configured to rotate about the shaft in a horizontal plane and vertically move along the shaft
the at least one filtration port includes a plurality of filtration ports which are provided in positions along the circumferential track which is made by the holding part along with rotation of the carrying arm.

8. The preprocessing apparatus according to claim 7, further comprising
a temperature adjustment port which contains the separation device or the collecting container containing a sample, and adjusts a temperature of the separation device or the collecting container at a certain temperature, the temperature adjustment port being provided in a position along the circumferential track which is made by the holding part along with rotation of the carrying arm.

9. The preprocessing apparatus according to claim 7, further comprising a disposal port for disposing of the separation device or the collecting container which is used, the disposal port being provided in a position along the circumferential track which is made by the holding part along with rotation of the carrying arm.

10. The preprocessing apparatus according to claim 1, wherein
a notch which is upwardly open is provided at an edge of an opening in an upper portion of the collecting container.

11. The preprocessing apparatus according to claim 1, wherein
the separation layer includes a deproteinizing filter for removing protein in a sample, or a deproteinizing filter and a prefilter which is provided above the deproteinizing filter and prevents clogging in the deproteinizing filter.

12. The preprocessing apparatus according to claim 1, wherein
the closed upper side of the skirt part is disposed above the separation layer.

13. The preprocessing apparatus according to claim 1, wherein
the separation device includes a flange part which is a circumferential expansion of an outer circumferential surface of the separation device, above the skirt part, and
the collecting container includes a flange part which is a circumferential expansion of an outer circumferential surface of a portion located above a portion fitted into the recess part forming the at least one filtration port.

14. The preprocessing apparatus according to claim 13, wherein
in the separation device, an outer diameter of a lower portion of the separation device which is a portion located below a base portion of the skirt part is smaller than an outer diameter of an upper portion of the separation device which is a portion located above the base portion of the skirt part, the flange part is provided in an outer circumferential surface of the upper portion of the separation device, and the lower portion of the separation device is contained in the collecting container,
in the collecting container, an outer diameter of an upper portion of the collecting container which is a portion into which the lower portion of the separation device is inserted is identical to the outer diameter of the upper portion of the separation device, and the flange part is provided in the upper portion of the collecting container, and
the flange part of the separation device and the flange part of the collecting container have the same shape and the same outer diameter.

15. An analysis system comprising:
the preprocessing apparatus according to claim 1;
a transfer apparatus which is provided in the preprocessing apparatus, and includes a transfer port for setting a collecting container containing a preprocessed sample with the carrying mechanism of the preprocessing apparatus, and a driving mechanism which moves the transfer port to an outside of the preprocessing apparatus; and
a liquid chromatograph system placed adjacent to the preprocessing apparatus, the liquid chromatograph system including:
an analytical flow path through which a mobile phase flows;
a sample injecting apparatus which takes a sample in the collecting container set in the transfer port which is placed outside the preprocessing apparatus by the transfer apparatus, and injects the sample into the analytical flow path;

an analytical column which is placed on the analytical flow path and separates the sample injected by the sample injecting apparatus into individual components; and a detector which detects a sample component separated in the analytical column.

* * * * *